US012742780B2

(12) United States Patent
Fahrmann et al.

(10) Patent No.: US 12,742,780 B2
(45) Date of Patent: Sep. 22, 2026

(54) METHODS FOR THE DETECTION AND TREATMENT OF OVARIAN CANCER

(71) Applicant: Board of Regents, The University of Texas System, Austin, TX (US)

(72) Inventors: Johannes Fahrmann, Houston, TX (US); Samir Hanash, Houston, TX (US)

(73) Assignee: Board of Regents, The University of Texas System, Austin, TX (US)

(*) Notice: Subject to any disclaimer, the term of this patent is extended or adjusted under 35 U.S.C. 154(b) by 770 days.

(21) Appl. No.: 18/297,979

(22) Filed: Apr. 10, 2023

(65) Prior Publication Data

US 2024/0044902 A1 Feb. 8, 2024

Related U.S. Application Data

(63) Continuation of application No. PCT/US2021/056852, filed on Oct. 27, 2021.

(60) Provisional application No. 63/107,160, filed on Oct. 29, 2020.

(51) Int. Cl.
*G01N 33/57545* (2026.01)

(52) U.S. Cl.
CPC ... *G01N 33/57545* (2026.01); *G01N 2800/50* (2013.01); *G01N 2800/52* (2013.01); *G01N 2800/56* (2013.01)

(58) Field of Classification Search
CPC ................................................ G01N 33/57449
USPC ......................................................... 435/7.23
See application file for complete search history.

(56) References Cited

U.S. PATENT DOCUMENTS

| | | | |
|---|---|---|---|
| 2007/0161059 | A1 | 7/2007 | Kawakita |
| 2008/0014211 | A1 | 1/2008 | Bot |
| 2012/0220476 | A1 | 8/2012 | Chan |
| 2014/0221240 | A1 | 8/2014 | Mansfield |
| 2015/0038522 | A1 | 2/2015 | Tanigawara |
| 2016/0362434 | A1 | 12/2016 | Pilkington |
| 2018/0311224 | A1 | 11/2018 | Hedley |
| 2020/0025766 | A1 | 1/2020 | Hanash |
| 2025/0138016 | A1 | 5/2025 | Hanash |

FOREIGN PATENT DOCUMENTS

| | | |
|---|---|---|
| CN | 109870579 | 6/2019 |
| WO | 2010148145 | 12/2010 |
| WO | 2015036781 | 3/2015 |
| WO | 2015064594 | 5/2015 |
| WO | 2017216025 | 12/2017 |
| WO | 2019178216 | 9/2019 |
| WO | 2022093960 | 5/2022 |
| WO | 2024020427 | 1/2024 |

OTHER PUBLICATIONS

Tockman et al (Cancer Res., 1992, 52:2711s-2718s).*

Fahrmann et al., "A MYC-Driven Plasma Polyamine Signature for Early Detection of Ovarian Cancer", Feb. 22, 2021 (Feb. 22, 2021), Cancers 2021, 13,913.

International Application No. PCT/US2021/056852; International Preliminary Report on Patentability, date of issuance May 11, 2023; 8 pages.

International Application No. PCT/US2021/056852; International Search Report and Written Opinion of the International Searching Authority, date of mailing Feb. 7, 2022; 10 pages.

Van Den Berg et al., "Determination of N-(3-acetamidopropyl)pyrrolidin-2-one, a metabolite of spermidine, in urine by isotope dilution mass fragmentography", (1986), Journal of Chromatography, 383 (1986) pp. 251-258.

Hilvo, M. et al., "Accumulated Metabolites of Hydroxybutyric Acid Serve as Diagnostic and Prognostic Biomarkers of Ovarian High-Grade Serous Carcinomas", Cancer Res., 76(4):796-804, (2016).

International Application No. PCT/US2023/070467; International Preliminary Report on Patentability, date of issuance Jan. 30, 2025; 8 pages.

International Application No. PCT/US2023/070467; International Search Report and Written Opinion of the International Searching Authority, date of mailing Mar. 11, 2024; 13 pages.

Irajizad, E. et al., "A Blood-Based Metabolite Panel for Distinguishing Ovarian Cancer from Benign Pelvic Masses", Clin Cancer Res., 28(21):4669-76, (2022).

Niemi, R. et al., "Urinary Polyamines as Biomarkers for Ovarian Cancer", Int J Gynecol Cancer, 27(7):1360-6, (2017).

Peretz, H. et al., "Urine metabolomics reveals novel physiologic functions of human aldehyde oxidase and provides biomarkers for typing xanthinuria", Metabolomics, (8):951-9, (2012).

* cited by examiner

*Primary Examiner* — Sean E Aeder

(74) *Attorney, Agent, or Firm* — Cynthia D. Hathaway; Michael Sertic

(57) ABSTRACT

Provided are methods and related kits for detection of early stage ovarian cancer, and determination of being at risk for ovarian cancer.

17 Claims, 9 Drawing Sheets

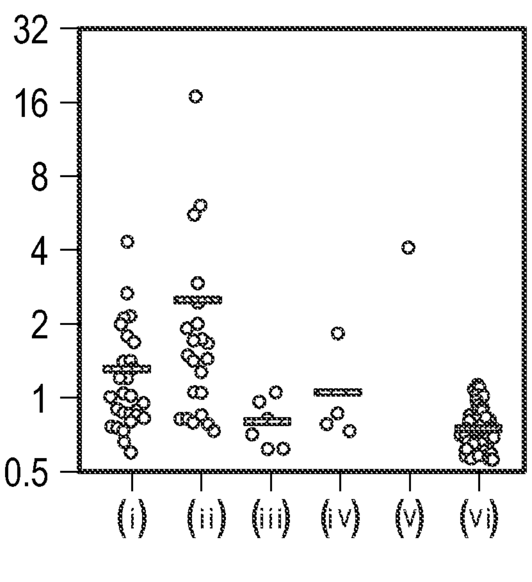
FIG. 7A
8
4
2
1
0.5
(i) (ii) (iii) (iv) (v) (vi)
FIG. 7B
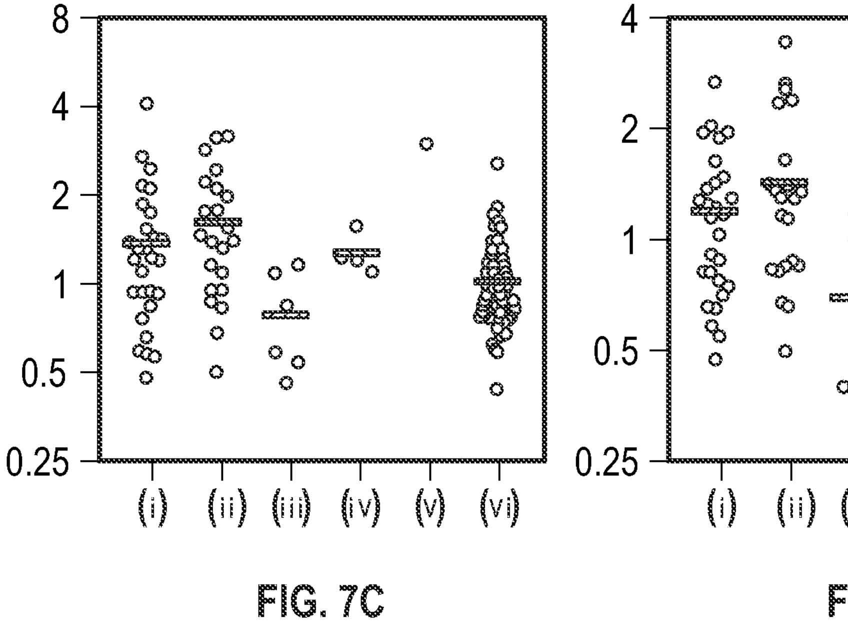
FIG. 7C
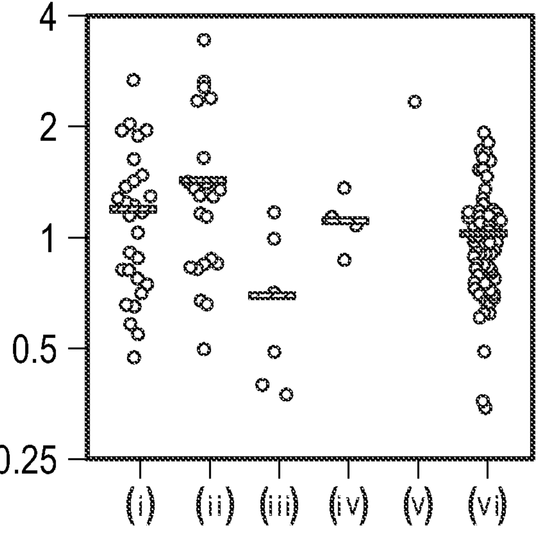
FIG. 7D

METHODS FOR THE DETECTION AND TREATMENT OF OVARIAN CANCER

CROSS REFERENCE TO RELATED APPLICATIONS

This application is a bypass continuation of International Application No. PCT/US2021/056852, filed Oct. 27, 2021, which claims the benefit of U.S. Provisional Patent Application No. 63/107,160, filed Oct. 29, 2020, the disclosures of each are hereby incorporated by reference as if written herein in their entireties.

BACKGROUND

Ovarian cancer represents a particularly insidious type of cancer, due to the failure of current methods to detect early-stage ovarian cancer adequately. Ovarian cancer that is detected early (Stage IA/IB/IC) has at least an 85% five-year survival rate; however, the prognosis worsens steeply with disease progression: the relative survival rate for stage IV cancer is 17%. Currently, over 70% of patients with ovarian cancer present with advanced stage (III-IV) disease, with dismal 5-year survival rates of less than 30%. Survival rates up to 70-90% can, however, be achieved with conventional surgery and chemotherapy, when disease is localized to the ovary (stage I) or pelvis (Stage II).

To date, CA125 is the most investigated ovarian cancer early detection marker. However, the sensitivity of CA125 remains limited and 20% of epithelial ovarian cancers do not express significant levels of CA125. Neither CA125 nor transvaginal sonography (TVS) alone has adequate sensitivity or specificity for early detection. A two-stage strategy whereby rising CA125 prompts TVS in a limited fraction of women screened can achieve adequate specificity, but the sensitivity of CA125 is limited. Thus, there is a need for additional marker(s) to detect early stage disease that would complement the performance of CA125.

Ovarian cancer and triple-negative breast cancer (TNBC) share common genomic features including MYC copy-number amplification. MYC is an oncogenic driver in the pathogenesis of ovarian cancer. Regulation of polyamine metabolizing enzyme (PME) transcription by MYC in triple negative breast cancer, and the presence of a plasma polyamine signature is associated with TNBC development and progression, has been demonstrated. A plasma polyamine signature associated with ovarian cancer is herein demonstrated, as well as utilization of polyamines in combination with CA125 for improved classification performance compared to CA125 alone.

SUMMARY

The present disclosure provides methods and kits for detecting and diagnosing ovarian cancer. The methods and kits use multiple assays of biomarkers contained within a biological sample obtained from a subject. The combined analysis of at least three biomarkers: DAS, N3AP, and CA125, provides high-accuracy detection of ovarian cancer.

A regression model was identified that can detect ovarian cancer in a subject based on the levels of DAS, N3AP, and CA125, or on the levels of DAS, N3AP, CA125, AcSpmd, and DiAcSpmd, that are found in a biological sample obtained from the subject.

Accordingly, provided herein are methods of detection of ovarian cancer in a subject, comprising measuring the levels of DAS, N3AP, and CA125, in a sample from the subject.

Also provided are methods of detection of ovarian cancer in a subject, comprising measuring the levels of DAS, N3AP, CA125, AcSpmd, and DiAcSpmd, in a sample from the subject.

Also provided are methods of treatment or prevention of ovarian cancer in a subject in whom the levels of DAS, N3AP, and CA125, or the levels of DAS, N3AP, CA125, AcSpmd, and DiAcSpmd, classify the subject as being at risk for ovarian cancer.

Also provided are corresponding kits for determining the presence of indicators for ovarian cancer in a sample from the subject, for determining the risk for ovarian cancer in a subject, and for determining and/or quantifying the risk for the ovarian cancer in a subject, comprising materials for measuring DAS, N3AP, and CA125 in the sample, or measuring the levels of DAS, N3AP, CA125, AcSpmd, and DiAcSpmd in the sample.

BRIEF DESCRIPTION OF THE DRAWINGS

FIG. 1A shows gene expression for ornithine decarboxylase 1 (ODC1) (P=0.04). FIG. 1B shows gene expression for spermine synthase (SMS) (P<0.0001). FIG. 1C shows gene expression for polyamine oxidase (PAOX) (P=0.01) in (i) normal ovarian tissue (n=8) and (ii) ovarian serous carcinomas (n=586) in the TCGA-ovarian cancer dataset. Vertical axis=$\log_2$ median-centered. Statistical significance was determined by 1-sided Wilcoxon rank sum test.

FIG. 2A shows relative fold change ($2^{-\Delta/\Delta}$ CT) of MYC (P<0.001), ODC1 (P<0.001), SRM (P<0.001), and SMS (P<0.001), following siRNA-mediated knockdown of MYC in serous carcinoma cell line SKOv3. (i) siCtrl (ii) siMYC-1 (iii) siMYC-3. Statistical significance was determined by 2-sided student t-test in comparison to siCtrl. FIG. 2B shows levels (area units±StDev) of DAS (P=0.04) in conditioned media of SKOv3 following siRNA-mediated knockdown of MYC. Vertical axis=area units±stdev. Statistical significance was determined by 2-sided student t-test.

FIG. 5A shows area under the curve (AUC) for the 3-marker panel consisting of (i) DAS+N3AP+CA125 and (ii) CA125 only. Horizontal axis=specificity (%); vertical axis=sensitivity (%). FIG. 5B shows a scatter plot illustrating the distribution of the 3-marker panel scores (vertical axis) and $\log_{10}$ CA125 values (horizontal axis) for (i) ovarian cancer cases (ii)

controls with benign diseases (iii) healthy controls. Broken lines represent 99% specificity cutoffs.

Figures 6A, 6B:
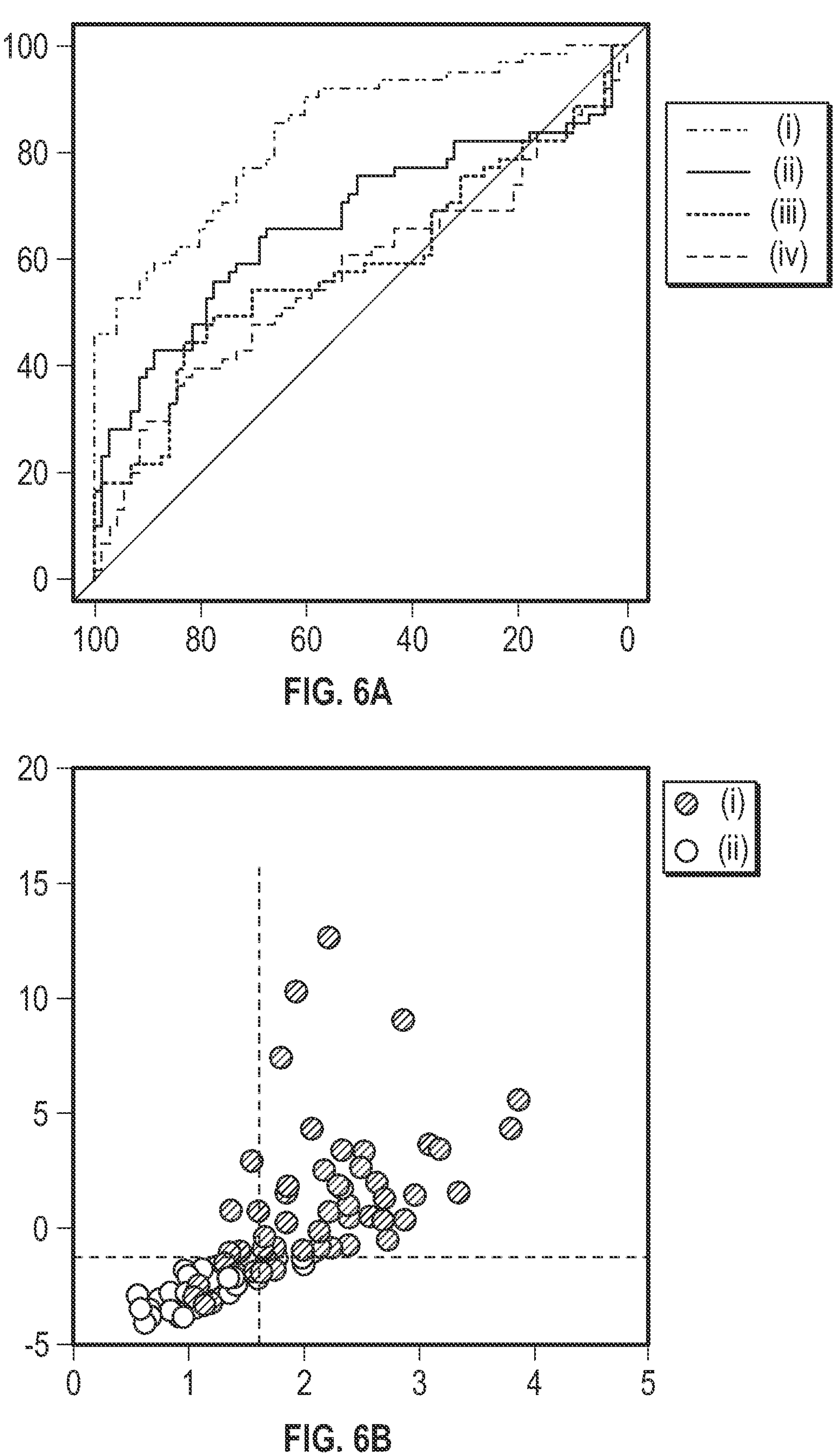

FIG. 6A-FIG. 6B. FIG. 6A depicts classification performances of plasma polyamines (i) DAS (ii) AcSpmd (iii) N3AP (iv) DiAcSpmd against validation Set #2. Area under the curve (AUC) of individual polyamines for delineating all cases (n=61) from healthy controls (n=71). FIG. 6B depicts a scatter plot illustrating the distribution of the 3-marker panel scores (vertical axis) and $\log_{10}$ CA125 values (horizontal axis) for (i) ovarian cancer cases (ii) healthy controls. Broken lines represent >99% specificity cutoffs.

FIG. 7A-FIG. 7D depict plasma levels of polyamines DAS (FIG. 7A), DiAcSpmd (FIG. 7B), AcSpmd (FIG. 7C), and N3AP (FIG. 7D) in cases stratified by histology and controls against validation Set #2. (i) Serous (n=28) (ii) endometrioid (n=22) (iii) mucinous (n=6) (iv) clear cell carcinoma (n=4) (v) other (n=1) (vi) healthy controls (n=71). Vertical axis=standardized values.

Figure 8:
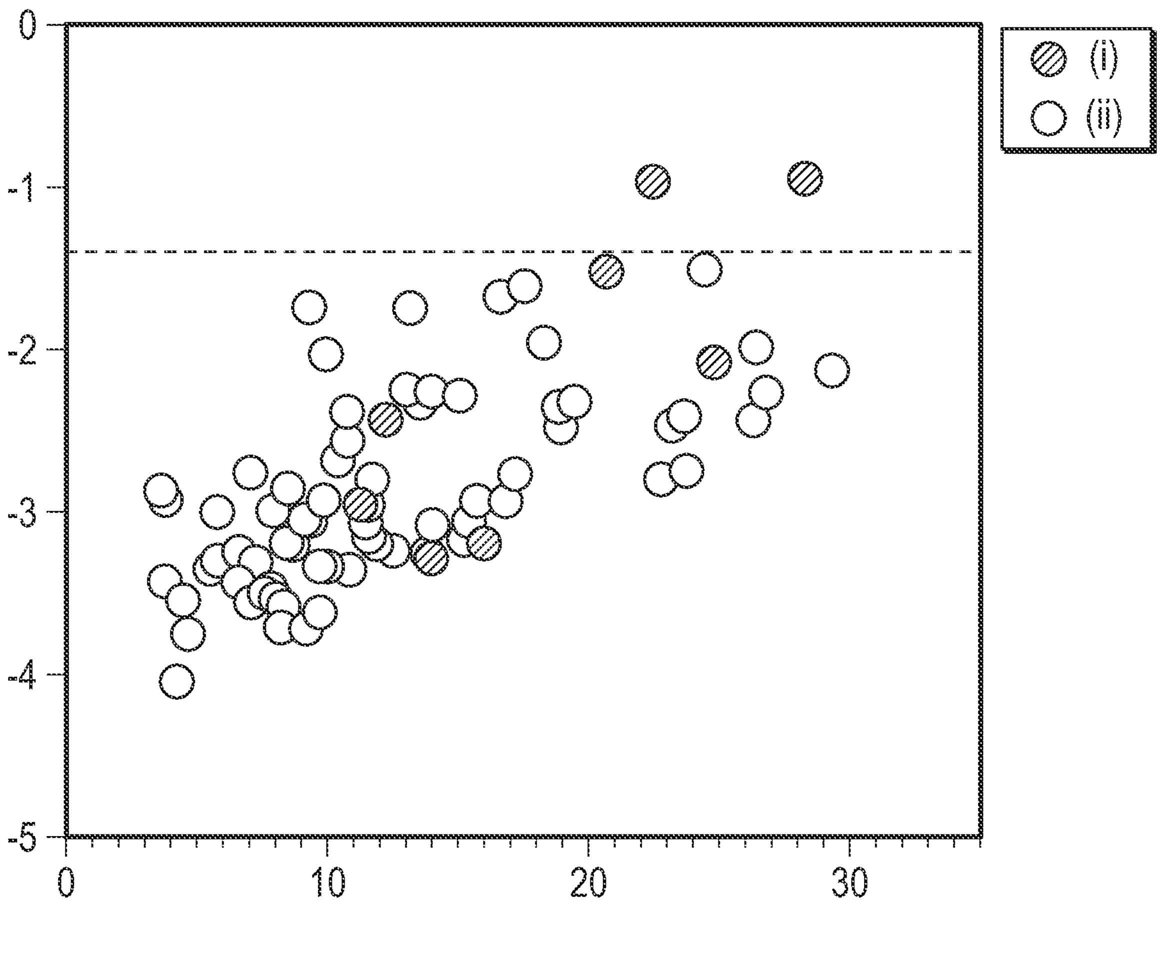

FIG. 8 depicts a scatter plot of 3-marker panel scores (vertical axis) and CA125 values (horizontal axis, U/mL) in CA125 'negative' (defined as <35 U/mL) subjects against validation Set #2 for (i) ovarian cancer cases (ii) healthy controls. Dashed line represents 100% specificity cutoff.

Figure 9A:
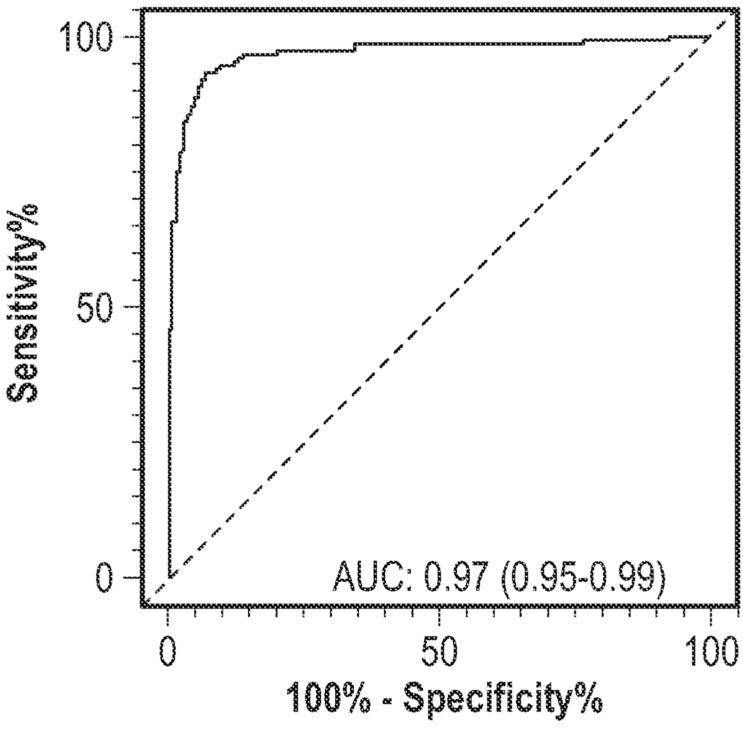
Figure 9B:
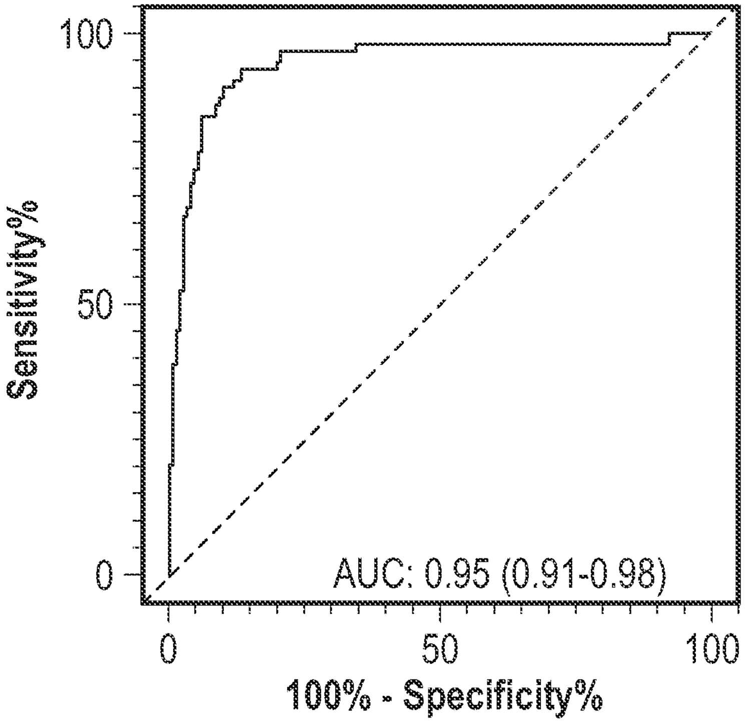

FIG. 9A-FIG. 9B depict the predictive performance of the fixed 3-marker panel (3MP) for distinguishing all OvCa cases (FIG. 9A) or early stage OvCa cases (FIG. 9B) from healthy controls.

DETAILED DESCRIPTION

Disclosed herein is an oncogenic MYC-driven plasma polyamine signature for early detection of ovarian cancer. Importantly, this polyamine signature can be combined with CA125 to further improve classifier performance. Specifically, a 3-marker panel consisting of DAS+N3AP+CA125 that was developed using early stage ovarian cancer cases and control subjects from the initial test set. The fixed 3-marker panel was then tested using an independent set of plasma samples consisting of 61 newly diagnosed early stage ovarian cancer cases and 71 healthy controls (Test Cohort #2), the results of which demonstrated marked improvement over CA125 alone by capturing 30% of cases missed by CA125 alone. Thus, a MYC-driven plasma polyamine signature associated with ovarian cancer was identified that complemented CA125 in detecting early stage ovarian cancer. In addition, a panel of 5 markers, including DAS, N3AP, CA125, AcSpmd, and DiAcSpmd, was tested for its predictive performance, as well as the 3-marker panel described herein, using fixed coefficients in an independent dataset consisting of 219 newly-diagnosed ovarian cancer cases (59 stage I+II and 160 stage III+IV), 190 individuals with benign pelvic masses (BPM), and 409 healthy controls.

In some embodiments, biomarkers are measured in blood samples drawn from subjects. In some embodiments, the presence or absence or, alternatively, the quantity, of biomarkers in a biological sample can be determined. In some embodiments, the level of biomarkers in a biological sample can be quantified.

In another embodiment, the measured concentrations are used to calculate a biomarker score based on sensitivity and specificity values at a cutoff set forth in Table 12. In another embodiment, such methods further comprise comparing the amount of DAS+N3AP+CA125 with a cutoff value as exemplified in Table 12. In another embodiment, such methods further comprise comparing the amount of DAS+N3AP+CA125+AcSpmd+DiAcSpmd with a cutoff value as exemplified in Table 14. In another embodiment, the cutoff value comprises an AUC (95% CI) of at least 0.89 (95% CI: 0.82-0.95). In another embodiment, the cutoff value comprises an AUC (95% CI) of from about 0.52 to about 0.95. In other embodiments, the cutoff value for N3AP comprises an AUC (95% CI) of at least 0.62, or the cutoff value for AcSpmd comprises an AUC (95% CI) of at least 0.75, or the cutoff value for DiAcSpmd comprises an AUC (95% CI) of at least 0.73, or the cutoff value for DAS comprises an AUC (95% CI) of at least 0.92. In another embodiment, the classification of the subject as having ovarian cancer has a sensitivity of 93% and 84% at 78% and 94% specificity, respectively.

In some embodiments, a surface is provided to analyze a biological sample. In some embodiment, biomarkers of interest adsorb nonspecifically onto this surface. In some embodiments, receptors specific for biomarkers of interest are incorporated onto this surface. In some embodiments, the surface is associated with a particle, for example, a bead.

In some embodiments, the biomarker binds to a particular receptor molecule, and the presence or absence or, alternatively, the quantity, of the biomarker-receptor complex can be determined. In some embodiments, the amount of biomarker-receptor complex can be quantified. In some embodiments, the receptor molecule is linked to an enzyme to facilitate detection and quantification.

In some embodiments, the biomarker binds to a particular relay molecule, and the biomarker-relay molecule complex in turn binds to a receptor molecule. In some embodiments, the presence or absence or, alternatively, the quantity, of the biomarker-relay-receptor complex can be determined. In some embodiments, the amount of biomarker-relay-receptor complex can be quantified. In some embodiments, the receptor molecule is linked to an enzyme to facilitate detection and quantification.

In some embodiments, a biological sample is analyzed sequentially for individual biomarkers. In some embodiments, a biological sample is divided into separate portions to allow for simultaneous analysis for multiple biomarkers. In some embodiments, a biological sample is analyzed in a single process for multiple biomarkers.

In some embodiments, the absence or presence of biomarker can be determined by visual inspection. In some embodiments, the quantity of biomarker can be determined by use of a spectroscopic technique. In some embodiments, the spectroscopic technique is mass spectrometry. In some embodiments, the spectroscopic technique is UV/Vis spectrometry. In some embodiments, the spectroscopic technique is an excitation/emission technique such as fluorescence spectrometry. In some embodiments, the spectroscopic technique is mass spectrometry. In some embodiments, the spectroscopic technique is combined with a chromatographic technique. In some embodiments, the chromatographic technique is liquid chromatography. In some embodiments, the chromatographic technique is high-performance liquid chromatography ("HPLC"). In some embodiments, the chromatographic technique is gas chromatography ("GC"). In some embodiments, the combined chromatographic/spectroscopic technique is high-performance liquid chromatography/mass spectrometry ("HPLC-MS"). In some embodiments, the combined chromatographic/spectroscopic technique is ultra high-performance liquid chromatography/mass spectrometry ("UPLC-MS").

In some embodiments, the analysis of biomarkers DAS, N3AP, and CA125, or analysis of biomarkers DAS, N3AP, CA125, AcSpmd, and DiAcSpmd, can be combined with analysis of additional biomarkers. In some embodiments, the additional biomarkers can be protein biomarkers. In some embodiments, the additional biomarkers can be non-protein biomarkers.

In some embodiments, a kit is provided for analysis of a biological sample. In some embodiments, the kit can contain the chemicals and reagents required to perform the analysis. In some embodiments, the kit contains a means for manipulating biological samples in order to minimize the required operator intervention. In some embodiments, the kit can record the outcome of an analysis digitally. In some embodiments, the kit can perform any needed mathematical processing of data generated by the analysis.

In another aspect, the disclosure provides a method of determining the risk for ovarian cancer in a subject, utilizing a biomarker panel and a protein marker panel wherein the biomarker panel comprises DAS, N3AP, and CA125, or comprises DAS, N3AP, CA125, AcSpmd, and DiAcSpmd; wherein the method comprises performing the following steps on a biological sample obtained from the subject; measuring the levels of the biomarkers and the protein biomarkers in the biological sample; wherein the amount of the biomarkers and the protein biomarkers determines the risk for ovarian cancer in the subject.

In another aspect, the disclosure provides a kit for a method as described herein, comprising a first reagent solution that comprises a first solute for detection of DAS, a second reagent solution that comprises a second solute for detection of N3AP, and a third reagent solution that comprises a third solute for detection of CA125. In other embodiments, reagent solutions are provided comprising solutes for detection of DAS, N3AP, CA125, AcSpmd, and DiAcSpmd.

In one embodiment, such a kit comprises a device for contacting the reagent solutions with a biological sample. In another embodiment, such a kit comprises at least one surface with means for binding at least one biomarker. In another embodiment, the at least one biomarker is selected from the group consisting of DAS, N3AP, and CA125, or consisting of DAS, N3AP, CA125, AcSpmd, and DiAcSpmd.

In another aspect, the disclosure provides a method of treating a subject suspected of risk for ovarian cancer, comprising: analyzing the subject for risk for ovarian cancer with a method as described herein and administering a therapeutically effective amount of a treatment for the ovarian cancer. In one embodiment, the treatment is surgery, chemotherapy, radiation therapy, targeted therapy, or a combination thereof. In another embodiment, such a method comprises at least one receptor molecule that selectively binds to a biomarker selected from the group consisting of DAS, N3AP, and CA125, or from the group consisting of DAS, N3AP, CA125, AcSpmd, and DiAcSpmd. In another embodiment, detection of the amount of DAS, N3AP, and CA125, or the amounts of DAS, N3AP, CA125, AcSpmd, and DiAcSpmd, comprises the use of a solid particle. In another embodiment, the solid particle is a bead. In another embodiment, at least one of the reporter molecules is linked to an enzyme. In another embodiment, at least one of the protein or metabolite markers generates a detectable signal. In another embodiment, the detectable signal is detectable by a spectrometric method. In another embodiment, the spectrometric method is mass spectrometry. In another embodiment, such a method comprises inclusion of patient history information into the assignment of being at risk for ovarian cancer or not being at risk for ovarian cancer. In another embodiment, such a method comprises administering at least one alternate diagnostic test for a patient assigned as being at risk for ovarian cancer.

In another aspect, the disclosure provides a method of treatment or prevention of ovarian cancer in a subject in whom the levels of DAS, N3AP, and CA125, or the levels of DAS, N3AP, CA125, AcSpmd, and DiAcSpmd, identifies a risk for ovarian cancer in the subject, comprising one or more steps of: administering a chemotherapeutic drug to the subject with ovarian cancer; administering therapeutic radiation to the subject with ovarian cancer; and surgery for partial or complete surgical removal of cancerous tissue in the subject with ovarian cancer. In one embodiment, the levels of DAS, N3AP, and CA125, or the levels of DAS, N3AP, CA125, AcSpmd, and DiAcSpmd, are elevated. In another embodiment, the levels of DAS, N3AP, and CA125, or the levels of DAS, N3AP, CA125, AcSpmd, and DiAcSpmd, are elevated in comparison to the levels of DAS, N3AP, and CA125, or DAS, N3AP, CA125, AcSpmd, and DiAcSpmd, in a reference subject or group that is not at risk for ovarian cancer. In another embodiment, the reference subject or group is healthy.

In another aspect, the disclosure provides a method of treatment or prevention of ovarian cancer in a subject in whom the levels of DAS, N3AP, and CA125, or the levels of DAS, N3AP, CA125, AcSpmd, and DiAcSpmd, identifies the subject as having or being at risk for ovarian cancer comprising one or more of: administering a chemotherapeutic drug to the subject with ovarian cancer; administering therapeutic radiation to the subject with ovarian cancer; and surgery for partial or complete surgical removal of cancerous tissue in the subject with ovarian cancer. In one embodiment, the levels of DAS, N3AP, and CA125, or the levels of DAS, N3AP, CA125, AcSpmd, and DiAcSpmd, are elevated. In another embodiment, the levels of DAS, N3AP, and CA125, or the levels of DAS, N3AP, CA125, AcSpmd, and DiAcSpmd, are elevated in comparison to the levels of DAS, N3AP, and CA125, or to the levels of DAS, N3AP, CA125, AcSpmd, and DiAcSpmd, in a reference subject or group that is not at risk for ovarian cancer. In another embodiment, the reference subject or group is healthy. In another embodiment, the subject is at high risk for ovarian cancer.

In another aspect, the disclosure provides a method of treating a subject suspected of risk for ovarian cancer, comprising analyzing the subject for risk for ovarian cancer with a method as disclosed herein; administering a therapeutically effective amount of a treatment for the ovarian cancer. In one embodiment, the treatment is surgery, chemotherapy, radiation therapy, targeted therapy, or a combination thereof.

In some embodiments, the amount of biomarker is determined with spectroscopy. In some embodiments, the spectroscopy that is utilized is UV-visible spectroscopy. In some embodiments, the spectroscopy that is utilized is mass spectrometry. In other embodiments, the spectroscopy that is utilized is nuclear magnetic resonance (NMR) spectroscopy, such as including, but not limited to, proton NMR spectroscopy, nuclear magnetic resonance (NMR) spectrometry, gas chromatography-mass spectrometry (GC-MS), liquid chromatography-mass spectrometry (LC-MS), correlation spectroscopy (COSy), nuclear Overhauser effect spectroscopy (NOESY), rotating frame nuclear Overhauser effect spectroscopy (ROESY), LC-TOF-MS, LC-MS/MS, and capillary electrophoresis-mass spectrometry.

The quantity of biomarker or biomarkers that is found in a particular assay can be directly reported to an operator, or alternately it can be stored digitally and readily made available for mathematical processing. A system can be provided for performing mathematical analysis, and can further report classification as ovarian cancer-positive or ovarian cancer-negative to an operator.

In some embodiments, additional assays known to those of ordinary skill in the art can function with the disclosure herein. Other assays include, but are not limited to, assays utilizing mass-spectrometry, immunoaffinity LC-MS/MS, surface plasmon resonance, chromatography, electrochemistry, acoustic waves, immunohistochemistry and array technologies.

The various system components discussed herein may include one or more of the following: a computer comprising one or more processors for processing digital data; short- or long-term digital memory; an input analog-to-digital converter for providing digitized data; an application program made available to the processor for directing processing of digital data by the processor; an input device for collecting information from the subject or operator, and an output device for displaying information to the subject or operator.

Also provided herein are methods of treatment for subjects who are classified as ovarian cancer-positive. Treatment for ovarian cancer-positive patients can include, but is not limited to, surgery, chemotherapy, radiation therapy, targeted therapy, or a combination thereof.

With regard to the detection of the biomarkers detailed herein, the disclosure is not limited to the specific biomolecules reported herein. In some embodiments, other biomolecules can be chosen for the detection and analysis of the disclosed biomarkers including, but not limited to, biomolecules based on proteins, antibodies, nucleic acids, aptamers, and synthetic organic compounds. Other molecules may demonstrate advantages in terms of sensitivity, efficiency, speed of assay, cost, safety, or ease of manufacture or storage. In this regard, those of ordinary skill in the art will appreciate that the predictive and diagnostic power of the biomarkers disclosed herein may extend to the analysis of not just the protein form of these biomarkers, but other representations of the biomarkers as well (e.g., nucleic acid). Further, those of ordinary skill in the art will appreciate that the predictive and diagnostic power of the biomarkers disclosed herein can also be used in combination with an analysis of other biomarkers associated with ovarian cancer. In some embodiments, other biomarkers associated with ovarian cancer can be protein-based biomarkers.

The disclosure additionally sets forth the following embodiments:

In one aspect, the disclosure provides a method of:

determining the risk of a subject for harboring ovarian cancer, predicting a predisposition to ovarian cancer in a subject, diagnosing ovarian cancer in a subject, classifying a subject as harboring/being at risk of harboring ovarian cancer or predicting the likelihood of progression of ovarian cancer in a subject, providing a prognosis for a subject with ovarian cancer, or selecting a subject with ovarian cancer for treatment with an anticancer therapy, comprising, in a biological sample obtained from the subject, a) measuring the levels of diacetylspermine (DAS), N-(3-acetamidopropyl)pyrrolidin-2-one (N3AP), and cancer antigen 125 (CA125); and b) comparing the levels of DAS, N3AP, and CA125 in said sample with a reference value corresponding to a healthy subject, wherein an altered amount of DAS, N3AP, and CA125 relative to said reference provides an indication selected from the group consisting of:

an indication that the subject harbors or is at risk of harboring ovarian cancer, or does not harbor or is not at risk of harboring ovarian cancer, an indication that the subject is at risk of developing ovarian cancer or not at risk of developing ovarian cancer, an indication of a predisposition of the subject to ovarian cancer, an indication of the likelihood of progression of the ovarian cancer in the subject, an indication of progression-free survival of the subject, an indication of the likely outcome of treatment of the ovarian cancer, and an indication that the subject is a candidate for treatment with an anticancer therapy.

In some embodiments, a method as described herein further comprises measuring the levels of N3AP, AcSpmd, and/or DiAcSpmd.

In some embodiments, the levels of DAS, N3AP, CA125, AcSpmd, and DiAcSpmd are elevated relative to the reference value.

In some embodiments, the levels of DAS, N3AP, CA125, AcSpmd, and DiAcSpmd are elevated relative to the corresponding levels in a biological sample obtained from a subject without ovarian cancer.

In some embodiments, the levels of DAS, N3AP, CA125, AcSpmd, and DiAcSpmd are elevated relative to the corresponding levels in a biological sample obtained from a subject with one or more benign pelvic masses.

In some embodiments, the biological sample is derived from the blood of the subject.

In some embodiments, the biological sample is serum.

In some embodiments, the ovarian cancer is chosen from serous and non-serous.

In some embodiments, the ovarian cancer is serous.

In some embodiments, the ovarian cancer is non-serous.

In some embodiments, the non-serous ovarian cancer is chosen from endometrioid, mucinous, and clear cell carcinoma.

In some embodiments, the ovarian cancer is early (e.g., stage I).

In some embodiments, the ovarian cancer is advanced (e.g., stage II).

In some embodiments, the ovarian cancer is epithelial in origin.

In some embodiments, the subject has an amplification in c-myc.

In some embodiments, the concentration of CA125 is determined by an immunoassay.

In some embodiments, the immunoassay uses an anti-CA125 antibody or binding fragment thereof.

In some embodiments, the concentration of at least one of DAS, N3AP, AcSpmd, and DiAcSpmd is determined by a method that comprises mass spectrometry.

In some embodiments, the concentration of at least one of DAS, N3AP, AcSpmd, and DiAcSpmd is determined by a method that comprises liquid chromatography.

In some embodiments, the concentrations of DAS, N3AP, AcSpmd, and DiAcSpmd are determined by a method that comprises mass spectrometry.

In some embodiments, the concentrations of DAS, N3AP, AcSpmd, and DiAcSpmd are determined by a method that comprises mass spectrometry.

In some embodiments, the concentrations of DAS, N3AP, AcSpmd, and DiAcSpmd are determined by a method that comprises both liquid chromatography and mass spectrometry.

In some embodiments, the method provides improved sensitivity at a given specificity compared to a method assessing DAS alone.

In some embodiments, the method provides improved sensitivity at a given specificity compared to a method assessing CA125 alone.

In some embodiments, the method provides improved sensitivity at about 99% specificity.

In some embodiments, the method correctly identifies more early-stage ovarian cancers than a method assessing DAS or CA125 alone.

In another aspect, the disclosure provides a diagnostic panel for ovarian cancer comprising DAS, N3AP, and CA125.

In some embodiments, the diagnostic panel has an AUC point estimate of greater than 0.82.

In some embodiments, the diagnostic panel has an AUC point estimate of about 0.84.

In some embodiments, the diagnostic panel has an AUC point estimate of about 0.97 for distinguishing ovarian cancer from healthy controls.

In some embodiments, the diagnostic panel has an AUC point estimate of about 0.95 for distinguishing early-stage ovarian cancer.

In another aspect, the disclosure provides a diagnostic panel for ovarian cancer comprising DAS, N3AP, AcSpmd, DiAcSpmd, and CA125.

In some embodiments, the diagnostic panel has an AUC point estimate of greater than 0.82.

In some embodiments, the diagnostic panel has an AUC point estimate of about 0.84.

In some embodiments, the diagnostic panel has an AUC point estimate of about 0.97 for distinguishing ovarian cancer from healthy controls.

In some embodiments, the diagnostic panel has an AUC point estimate of about 0.95 for distinguishing early-stage ovarian cancer.

In some embodiments, DAS, N3AP, AcSpmd, DiAcSpmd, and CA125 are evaluated using fixed coefficients.

In some embodiments, the method further comprises comparing the amount of DAS, N3AP, CA125, AcSpmd, and DiAcSpmd with a cutoff value comprising an AUC (95% CI) of from about 0.52 to about 0.95.

In some embodiments, the cutoff value for N3AP comprises an AUC (95% CI) of at least 0.62.

In some embodiments, the cutoff value for AcSpmd comprises an AUC (95% CI) of at least 0.75.

In some embodiments, the cutoff value for DiAcSpmd comprises an AUC (95% CI) of at least 0.73.

In some embodiments, the cutoff value for DAS comprises an AUC (95% CI) of at least 0.92.

In another aspect, the disclosure provides a method of treatment or prevention of progression of ovarian cancer in a subject in whom the levels of DAS, N3AP, and CA125 are elevated relative to reference values corresponding to levels in subjects without ovarian cancer, comprising one or more of:

- administering an anticancer drug to the subject with ovarian cancer;
- administering therapeutic radiation to the subject with ovarian cancer; and
- surgery for partial or complete surgical removal of cancerous tissue in the subject with ovarian cancer.

In another aspect, the disclosure provides a method of treatment or prevention of progression of ovarian cancer in a subject in whom the levels of DAS, N3AP, CA125, AcSpmd, and DiAcSpmd are elevated relative to reference values corresponding to levels in subjects without ovarian cancer, comprising one or more of:

- administering an anticancer drug to the subject with ovarian cancer;
- administering therapeutic radiation to the subject with ovarian cancer; and The foregoing has outlined rather broadly the features and technical benefits of the disclosure in order that the detailed description may be better understood. It should be appreciated by those skilled in the art that the specific embodiments disclosed may be readily utilized as a basis for modifying or designing other structures or processes for carrying out the same purposes of the disclosure. It is to be understood that the present disclosure is not limited to the particular embodiments described, as variations of the particular embodiments may be made and still fall within the scope of the appended claims.

Abbreviations and Definitions

As used herein, the terms below have the meanings indicated.

When ranges of values are disclosed, and the notation "from n1 . . . to n2" or "between n1 . . . and n2" is used, where n1 and n2 are the numbers, then unless otherwise specified, this notation is intended to include the numbers themselves and the range between them. This range may be integral or continuous between and including the end values. By way of example, the range "from 2 to 6 carbons" is intended to include two, three, four, five, and six carbons, since carbons come in integer units. Compare, by way of example, the range "from 1 to 3 μM (micromolar)," which is intended to include 1 μM, 3 μM, and everything in between to any number of significant figures (e.g., 1.255 μM, 2.1 μM, 2.9999 μM, etc.).

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

Any definition herein may be used in combination with any other definition to describe a composite structural group. By convention, the trailing element of any such definition is that which attaches to the parent moiety. For example, the composite group alkylamido would represent an alkyl group attached to the parent molecule through an amido group, and the term alkoxyalkyl would represent an alkoxy group attached to the parent molecule through an alkyl group.

As used herein, "ovarian cancer" refers to a malignant growth of cells that forms in the ovary. Ovarian cancer is most commonly epithelial in origin (around 90% of ovarian cancers), and can be classified into a variety of types, including serous and non-serous ovarian cancer. Serous ovarian cancer is the most common type of epithelial cell ovarian cancer and accounts for around 40% of all ovarian cancers, while non-serous ovarian cancer may include, but is not limited to, endometrioid, mucinous, and clear cell carcinoma. In some embodiments, ovarian cancer may vary in severity, represented by stages I through IV. In some embodiments, ovarian cancer may be in an early stage (e.g., stage I), or it may be advanced (e.g., stage II, III, or IV).

As used herein, "c-MYC" refers to the c-MYC oncogene, the expression of which is found to be upregulated in up to 70% of human cancers. c-MYC is on chromosome 8924, which is frequently translocated or amplified in cancer. Thus, in some embodiments, a subject having ovarian cancer may have a translocation or an amplification in the c-MYC gene. In other embodiments, a subject having ovarian cancer has an amplification in c-MYC.

When a group is defined to be "null," what is meant is that said group is absent.

As used herein, the terms "subject" or "patient" refer to a mammal, preferably a human, for whom a classification as ovarian cancer-positive or ovarian cancer-negative is desired, and for whom further treatment can be provided.

As used herein, a "reference patient," "reference subject," or "reference group" refers to a group of patients or subjects to which a test sample from a patient or subject suspected of having or being at risk for ovarian cancer may be compared. In some embodiments, such a comparison may be used to determine whether the test subject has ovarian cancer. A reference patient or group may serve as a control for testing or diagnostic purposes. As described herein, a reference patient or group may be a sample obtained from a single patient, or may represent a group of samples, such as a pooled group of samples.

As used herein, "healthy" refers to an individual in whom no evidence of ovarian cancer is found, i.e., the individual does not have ovarian cancer. Such an individual may be classified as "ovarian cancer-negative" or as having healthy ovaries, or normal, non-compromised ovarian function. A healthy patient or subject has no symptoms of ovarian cancer or other ovarian disease, but may have benign pelvic masses, i.e., a combination of adenomas and cysts. In some embodiments, a healthy patient or subject may be used as a reference patient for comparison to diseased or suspected diseased samples for determination of ovarian cancer in a patient or a group of patients.

As used herein, the terms "treatment" or "treating" refer to the administration of medicine or the performance of medical procedures with respect to a subject, for either prophylaxis (prevention) or to cure or reduce the extent of or likelihood of occurrence or recurrence of the infirmity or malady or condition or event in the instance where the subject or patient is afflicted. As related to the present disclosure, the term may also mean the administration of pharmacological substances or formulations, or the performance of non-pharmacological methods including, but not limited to, radiation therapy and surgery. Pharmacological substances as used herein may include, but are not limited to, anticancer drugs including chemotherapeutics, hormone therapies, and targeted therapies. Examples of chemotherapeutics for ovarian cancer include paclitaxel (e.g. albumin bound paclitaxel or nab-paclitaxel, trade name Abraxane®), altretamine (Hexalen®), capecitabine (Xeloda®), cyclophosphamide (Cytoxan®), etoposide (VP-16), gemcitabine (Gemzar®), ifosfamide (Ifex®), irinotecan (CPT-11, Camptosar®), liposomal irinotecan (Onivyde®), liposomal doxorubicin (Doxil®), melphalan, pemetrexed (Alimta®), topotecan, and vinorelbine (Navelbine®); as well as combination regimens of chemotherapy including cisplatin+paclitaxel, TIP (paclitaxel/Taxol, ifosfamide, and cisplatin/Platinol), VeIP (vinblastine, ifosfamide, and cisplatin/Platinol), VIP (etoposide/VP-16, ifosfamide, and cisplatin/Platinol), VAC (vincristine, dactinomycin, and cyclophosphamide), and PEB (cisplatin/Platinol, etoposide, and bleomycin); hormone therapies, including luteinizing-hormone-releasing hormone (LHRH) agonists (such as goserelin (Zoladex®) and leuprolide (Lupron®)), tamoxifen, aromatase inhibitors (such as letrozole (Femara®), anastrozole (Arimidex®), and exemestane (Aromasin®)), and targeted therapies such as angiogenesis inhibitors including bevacizumab (Avastin) as well as (poly(ADP)-ribose polymerase) (PARP) inhibitors such as Olaparib (Lynparza), rucaparib (Rubraca), and niraparib (Zejula). The terms "pharmacological substance" and "anticancer therapy" may also include substances used in immunotherapy, such as checkpoint inhibitors. Treatment may include a multiplicity of pharmacological substances, or a multiplicity of treatment methods, including, but not limited to, surgery and chemotherapy.

As used herein, "amount" or "level" refers to a typically quantifiable measurement for a biomarker described herein, wherein the measurement enables comparison of the marker between samples and/or to control samples. In some embodiments, an amount or level is quantifiable and refers to the levels of a particular marker in a biological sample (e.g., blood, serum, urine, etc), as determined by laboratory methods or tests such as an immunoassay, (e.g., antibodies), mass spectrometry, or liquid chromatography. In some embodiments, a marker may be present in the sample in an increased amount, or in a decreased amount. Marker comparisons may be based on direct measurement of the levels of a biomarker described herein, (e.g., through protein quantification or gene expression analysis) or may be based on measurement of e.g., reporter molecules, biomarker-receptor complexes, biomarker-relay-receptor complexes, or the like.

As used herein, the term "ELISA" refers to enzyme-linked immunosorbent assay. This assay generally involves contacting a fluorescently tagged sample of proteins with antibodies having specific affinity for those proteins. Detection of these proteins can be accomplished with a variety of means, including but not limited to laser fluorimetry.

As used herein, the term "regression" refers to a statistical method that can assign a predictive value for an underlying characteristic of a sample based on an observable trait (or set of observable traits) of said sample. In some embodiments, the characteristic is not directly observable. For example, the regression methods used herein can link a qualitative or quantitative outcome of a particular biomarker test, or set of biomarker tests, on a certain subject, to a probability that said subject is for ovarian cancer-positive.

As used herein, the term "logistic regression" refers to a regression method in which the assignment of a prediction from the model can have one of several allowed discrete values. For example, the logistic regression models used herein can assign a prediction, for a certain subject, of either ovarian cancer-positive or ovarian cancer-negative.

As used herein, the term "biomarker score" refers to a numerical score for a particular subject that is calculated by inputting the particular biomarker levels for said subject to a statistical method.

As used herein, the term "composite score" refers to a summation of the normalized values for the predetermined markers measured in the sample from the subject. In one embodiment, the normalized values are reported as a biomarker score and those biomarker score values are then summed to provide a composite score for each subjected tested. When used in the context of the risk categorization table and correlated to a stratified grouping based on a range of composite scores in the Risk Categorization Table, the "composite score" is used to determine the "risk score" for each subject tested wherein the multiplier indicating increased likelihood of having the cancer for the stratified grouping becomes the "risk score".

As used herein, the term "risk score" refers to a single numerical value that indicates an asymptomatic human subject's risk for ovarian cancer as compared to the known prevalence of ovarian cancer in the disease cohort. In certain embodiments, the composite score as calculated for a human subject and correlated to a multiplier indicating risk for ovarian cancer, wherein the composite score is correlated based on the range of composite scores for each stratified grouping in the risk categorization table. In this way the composite score is converted to a risk score based on the multiplier indicating increased likelihood of having the cancer for the grouping that is the best match for the composite score.

As used herein, the term "cutoff" or "cutoff point" refers to a mathematical value associated with a specific statistical method that can be used to assign a classification of ovarian cancer-positive of ovarian cancer-negative to a subject, based on said subject's biomarker score.

As used herein, when a numerical value above or below a cutoff value "is characteristic of ovarian cancer," what is meant is that the subject, analysis of whose sample yielded the value, either has ovarian cancer or is at risk for ovarian cancer.

As used herein, the "use" of markers for diagnosing ovarian cancer refers to quantification of the levels or amounts in a biological sample of one or more markers described herein. Quantification may be done using any known methods or techniques in the art or described herein. In some embodiments, markers may be used or combined together as a panel for statistical comparison to other samples.

In some embodiments, the amount or levels of DAS, N3AP, and CA125, or the amount or levels of DAS, N3AP, CA125, AcSpmd, and DiAcSpmd, are compared with a cutoff value comprising an AUC (95% CI) of from about 0.52 to about 0.95, e.g., about 0.52, about 0.53, about 0.54, about 0.55, about 0.56, about 0.57, about 0.58, about 0.59, about 0.60, about 0.61, about 0.62, about 0.63, about 0.64, about 0.65, about 0.66, about 0.67, about 0.68, about 0.69, about 0.70, about 0.71, about 0.72, about 0.73, about 0.74, about 0.75, about 0.76, about 0.77, about 0.78, about 0.79, about 0.80, about 0.81, about 0.82, about 0.83, about 0.84, about 0.85, about 0.86, about 0.87, about 0.88. about 0.89, about 0.90, about 0.91, about 0.92, about 0.93, about 0.94, about 0.95, about 0.96, about 0.97, about 0.98, about 0.99, or the like. In some embodiments, using markers DAS, N3AP, and CA125 together as a panel, or using markers DAS, N3AP, CA125, AcSpmd, and DiAcSpmd together as a panel may have an AUC (95% CI) of 0.90 or greater, including about 0.90, about 0.91, about 0.92, about 0.93, about 0.94, about 0.95, about 0.96, about 0.97, about 0.98, about 0.99, or the like.

In some embodiments, analyzing markers DAS, N3AP, and CA125 together as a panel for diagnosis of ovarian cancer using fixed coefficients, or analyzing markers DAS, N3AP, CA125, AcSpmd, and DiAcSpmd together as a panel for diagnosis of ovarian cancer using fixed coefficients may result in an AUC (95% CI) of from about 0.95 to about 0.99 for distinguishing ovarian cancer cases from healthy controls, e.g., about 0.95, about 0.96, about 0.97, about 0.98, about 0.99 or the like. In some embodiments, analyzing these marker panels using fixed coefficients may result in an AUC (95% CI) of 0.97 for distinguishing ovarian cancer cases from healthy controls. In some embodiments, analyzing any of the marker panels described herein for diagnosis of ovarian cancer using fixed coefficients may result in an AUC (95% CI) of from about 0.91 to about 0.98 for distinguishing early stage ovarian cancer, e.g., about 0.91, about 0.92, about 0.93, about 0.94, about 0.95, about 0.96, about 0.97, about 0.98, about 0.99 or the like. In some embodiments, analyzing these marker panels using fixed coefficients may result in an AUC (95% CI) of 0.95 for distinguishing early stage ovarian cancer.

In some embodiments, the cutoff value for N3AP comprises an AUC (95% CI) of at least 0.62, e.g., about 0.62, about 0.63, about 0.64, about 0.65, about 0.66, about 0.67, about 0.68, about 0.69, about 0.70, about 0.71, about 0.72, about 0.73, about 0.74, about 0.75, about 0.76, about 0.77, about 0.78, about 0.79, about 0.80, about 0.81, about 0.82, about 0.83, about 0.84, about 0.85, about 0.86, about 0.87, about 0.88. about 0.89, about 0.90, about 0.91, about 0.92, about 0.93, about 0.94, about 0.95, about 0.96, about 0.97, about 0.98, about 0.99, or the like.

In some embodiments, the cutoff value for AcSpmd comprises an AUC (95% CI) of at least 0.75, e.g., about 0.75, about 0.76, about 0.77, about 0.78, about 0.79, about 0.80, about 0.81, about 0.82, about 0.83, about 0.84, about 0.85, about 0.86, about 0.87, about 0.88. about 0.89, about 0.90, about 0.91, about 0.92, about 0.93, about 0.94, about 0.95, about 0.96, about 0.97, about 0.98, about 0.99, or the like.

In some embodiments, the cutoff value for DiAcSpmd comprises an AUC (95% CI) of at least 0.73, e.g., about 0.73, about 0.74, about 0.75, about 0.76, about 0.77, about 0.78, about 0.79, about 0.80, about 0.81, about 0.82, about 0.83, about 0.84, about 0.85, about 0.86, about 0.87, about 0.88. about 0.89, about 0.90, about 0.91, about 0.92, about 0.93, about 0.94, about 0.95, about 0.96, about 0.97, about 0.98, about 0.99, or the like.

In some embodiments, the cutoff value for DAS comprises an AUC (95% CI) of at least 0.92, e.g., about 0.92, about 0.93, about 0.94, about 0.95, about 0.96, about 0.97, about 0.98, about 0.99, or the like.

As used herein, a subject who is at "risk for ovarian cancer" is one who may not yet evidence overt symptoms of ovarian cancer, but who is producing levels of biomarkers which indicate that the subject has ovarian cancer, or may develop it in the near term. A subject who has ovarian cancer or is suspected of harboring ovarian cancer may be treated for the cancer or suspected cancer.

As used herein, the term "classification" refers to the assignment of a subject as being at risk for ovarian cancer or not being at risk for ovarian cancer, based on the result of the biomarker score that is obtained for said subject.

As used herein, the term "Wilcoxon rank sum test," also known as the Mann-Whitney U test, Mann-Whitney-Wilcoxon test, or Wilcoxon-Mann-Whitney test, refers to a specific statistical method used for comparison of two populations. For example, the test can be used herein to link an observable trait, in particular a biomarker level, to the absence or the risk for ovarian cancer in subjects of a certain population.

As used herein, the term "true positive rate" refers to the probability that a given subject classified as positive by a certain method is truly positive.

As used herein, the term "false positive rate" refers to the probability that a given subject classified as positive by a certain method is truly negative.

As used herein, the term "sensitivity" refers to, in the context of various biochemical assays, the ability of an assay to correctly identify those with a disease (i.e., the true positive rate). By comparison, as used herein, the term "specificity" refers to, in the context of various biochemical assays, the ability of an assay to correctly identify those without the disease (i.e., the true negative rate). Sensitivity and specificity are statistical measures of the performance of a binary classification test (i.e., classification function). Sensitivity quantifies the avoiding of false negatives, and specificity does the same for false positives.

As used herein, "fixed coefficients" or "fixed model coefficients" refers to a statistical method of standardizing coefficients in order to allow comparison of the relative importance of each coefficient in a regression model. In some embodiments, fixed coefficients involves using the same beta-coefficients from a logistic regression model to yield a composite score for the developed combination rule, which is ultimately used to make a clinical decision based on a decision threshold(s).

As used herein, a "sample" refers to a test substance to be tested for the presence of, and levels or concentrations thereof, of a biomarker as described herein. A sample may be any substance appropriate in accordance with the present disclosure, including, but not limited to, blood, blood serum, blood plasma, or any part thereof.

As used herein, a "metabolite" refers to small molecules that are intermediates and/or products of cellular metabolism. Metabolites may perform a variety of functions in a cell, for example, structural, signaling, stimulatory and/or inhibitory effects on enzymes. In some embodiments, a metabolite may be a non-protein, plasma-derived metabolite marker, such as including, but not limited to, AcSpmd, DiAcSpmd, DAS, and N3AP. In some embodiments, a metabolite useful as described herein may be a "polyamine," i.e., an organic compound having more than two amino groups. In some embodiments, a polyamine as described herein be a plasma polyamine. In some embodiments, polyamines useful for the present panels and methods include, but are not limited to, DAS, N3AP, AcSpmd, and DiAcSpmd. These polyamines may be combined with other markers, e.g., CA125, for enhanced detection of ovarian cancer as described herein.

As used herein, the term "3-marker panel" or "3MP" refers to a panel of 3 biomarkers, which includes DAS, N3AP, and CA125, useful for detecting ovarian cancer in a patient suspected of having ovarian cancer. In some embodiments, the 3-marker panel may be evaluated in combination with additional markers, such as plasma polyamines, to enhance detection of ovarian cancer in biological samples from patients suspected as having ovarian cancer. Useful plasma polyamines include, but are not limited to, N3AP, AcSpmd, DiAcSpmd, and/or DAS. Additional polyamines are known in the art and may be included as deemed appropriate by a clinician.

As used herein, the term "ROC" refers to receiver operating characteristic, which is a graphical plot used herein to gauge the performance of a certain diagnostic method at various cutoff points. A ROC plot can be constructed from the fraction of true positives and false positives at various cutoff points.

As used herein, the term "AUC" refers to the area under the curve of the ROC plot. AUC can be used to estimate the predictive power of a certain diagnostic test. Generally, a larger AUC corresponds to increasing predictive power, with decreasing frequency of prediction errors. Possible values of AUC range from 0.5 to 1.0, with the latter value being characteristic of an error-free prediction method.

As described herein, the levels of markers DAS, N3AP, and CA125 may be used as a diagnostic panel to diagnose ovarian cancer. In other embodiments, the levels of markers DAS, N3AP, CA125, AcSpmd, and DiAcSpmd may be used as a diagnostic panel to diagnose ovarian cancer. In some embodiments, one or both of these panels may be evaluated using fixed coefficients. In some embodiments, analyzing the levels of DAS, N3AP, and CA125, or the levels of DAS, N3AP, CA125, AcSpmd, and DiAcSpmd, for diagnosing ovarian cancer may produce an AUC point estimate of greater than about 0.82, e.g., about 0.82, about 0.83, about 0.84, about 0.85, about 0.86, about 0.87, about 0.88. about 0.89, about 0.90, about 0.91, about 0.92, about 0.93, about 0.94, about 0.95, about 0.96, about 0.97, about 0.98, about 0.99, or the like. In some embodiments, analyzing the levels of DAS, N3AP, and CA125, or the levels of DAS, N3AP, CA125, AcSpmd, and DiAcSpmd, for diagnosing ovarian cancer may produce an AUC point estimate of about 0.84.

In some embodiments, analyzing the levels of DAS, N3AP, and CA125, or the levels of DAS, N3AP, CA125, AcSpmd, and DiAcSpmd, for diagnosing ovarian cancer may have an AUC point estimate of about 0.97 for distinguishing ovarian cancer from healthy controls. In some embodiments, an AUC point estimate of about 0.95 may be obtained for distinguishing early-stage ovarian cancer (e.g., stage I).

As used herein, the term "p-value" or "p" refers to the probability that the distributions of biomarker scores for ovarian cancer-positive and ovarian cancer-negative subjects are identical in the context of a Wilcoxon rank sum test. Generally, a p-value close to zero indicates that a particular statistical method will have high predictive power in classifying a subject.

As used herein, the term "CI" refers to a confidence interval, i.e., an interval in which a certain value can be predicted to lie with a certain level of confidence. As used herein, the term "95% CI" refers to an interval in which a certain value can be predicted to lie with a 95% level of confidence.

As used herein, the term "disease progression" or "early disease progression" is defined as upgrading of Gleason score and/or increased tumor volume on surveillance biopsy within 18 months after start of active surveillance.

List of Abbreviations

AcSpmd=acetyl spermidine; AS=active surveillance; AUC=area under the curve; DAS=N1, N12-diacetylspermine; DiAcSpmd=N1,N8-diacetyl spermidine; FBS=fetal bovine serum; HILIC=hydrophilic interaction liquid chromatography; HPLC=high performance liquid chromatography; N3AP=N-(3-acetamidopropyl)pyrrolidin-2-one; ODC1=ornithine decarboxylase; PAOX=polyamine oxidase; ROC=receiver operating characteristic; SEM=standard error of the mean: SFM=serum-free media; SMS=spermine synthase; SRM=spermidine synthase; TCGA=The Cancer Genome Atlas; UPLC=ultra high performance liquid chromatography; UPLC/MS=ultra high performance liquid chromatography/mass spectrometry.

EXAMPLES

The following examples are included to demonstrate embodiments of the disclosure. The following examples are presented only by way of illustration and to assist one of ordinary skill in using the disclosure. The examples are not intended in any way to otherwise limit the scope of the disclosure. Those of skill in the art should, in light of the present disclosure, appreciate that many changes can be made in the specific embodiments which are disclosed and still obtain a like or similar result without departing from the spirit and scope of the disclosure.

Procedure 1: Metabolites

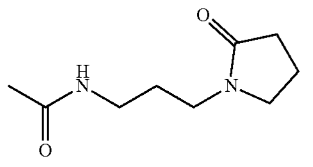

N-(3-acetamidopropyl)pyrrolidin-2-one ("N3AP")

Procedure 2: Human Cohorts

Plasma samples were drawn from the MD Anderson Gynecologic Cancer Bank and from the Normal Risk Ovarian Cancer Screening Study (NROSS). Ethical approval was obtained for these studies from the appropriate institutional review boards/ethic committees at MD Anderson and collaborating institutions. All participants had consent for the use of samples in ethically approved secondary studies. Plasmas from healthy controls were from the NROSS study who did not develop ovarian cancer. Over the last two decades, the NROSS trial has involved 6379 postmenopausal women over the age of 50 at average risk for developing ovarian cancer and who have been followed with annual CA125 measurements and who have been referred for transvaginal ultrasound and gynecological evaluation if CA125 values increase from each individual's baseline as judged by the Risk of Ovarian Cancer Algorithm (ROCA). All healthy controls were followed for a minimum of 7 years to ensure cancer-free status.

Test Set #1 (Table 1) consisted of 41 early stage (I-II) cases, 75 late stage (III-IV) cases, 71 healthy controls and 72 patients with benign pelvic masses.

TABLE 1

Patient characteristics for Test Set #1. Control #1 represented healthy subjects; Control #2 represent individuals with benign pelvic masses.

| | Test Set #1 | | |
|---|---|---|---|
| | Cases | Control #1 | Control #2 |
| Number of Subjects | 116 | 71 | 72 |
| Age (mean ± stdev) | 58 ± 13 | 69 ± 7 | 56 ± 13 |
| CA125 (u/mL), mean ± stdev | 789 ± 2110 | 13 ± 8 | 62 ± 125 |
| Serous | | | |
| Stage I, N (%) | 11 (9.5) | — | — |
| Stage II, N (%) | 5 (4.3) | — | — |
| Stage III, N (%) | 64 (55.2) | — | — |
| Stage IV, N (%) | 11 (9.5) | — | — |
| Non-Serous | | | |
| Endometriod | | | |
| Stage I, N (%) | 10 (8.6) | — | — |
| Stage II, N (%) | 2 (1.7) | — | — |
| Mucinous | | | |
| Stage I, N (%) | 3 (2.6) | — | — |
| Stage II, N (%) | 1 (0.9) | — | — |
| Clear Cell Carcinoma | | | |
| Stage I, N (%) | 6 (5.2) | — | — |
| Stage II, N (%) | 2 (1.7) | — | — |
| Other | | | |
| Transitional cell carcinoma (Stage I) | 1 (0.9) | — | — |

Validation Set #2 (Table 2) consisted of 61 early stage cases and 71 healthy controls.

TABLE 2

Patient characteristics for validation Set #2.

| | Validation Set #2 | |
|---|---|---|
| | Cases | Healthy Controls |
| Number of Subjects | 61 | 71 |
| Age (mean ± stdev) | 57 ± 15 | 65 ± 9 |
| CA125 (u/mL), mean ± stdev | 487 ± 1260 | 14 ± 9 |
| Serous | | |
| Stage I, N (%) | 13 (21.3) | — |
| Stage II, N (%) | 15 (24.6) | — |
| Non-Serous | | |
| Distinguish from N (%) | | |
| Stage I, N (%) | 16 (26.2) | — |
| Stage II, N (%) | 6 (9.8) | — |
| Mucinous, N (%) | | |
| Stage I, N (%) | 6 (9.8) | — |
| Clear Cell Carcinoma, N (%) | | |
| Stage I, N (%) | 3 (4.9) | — |
| Stage II, N (%) | 1 (1.6) | — |
| Other | | |
| transitional carcinoma (Stage II) | 1 (1.6) | — |

Procedure 3: Metabolomics Analysis

Plasma metabolites were extracted from pre-aliquoted EDTA plasma (10 μL) with 30 μL of LCMS grade methanol (ThermoFisher) in a 96-well microplate (Eppendorf). Plates were heat sealed, vortexed for 5 min at 750 rpm, and centrifuged at 2000×g for 10 min at room temperature. The supernatant (10 μL) was carefully transferred to a 96-well plate, leaving behind the precipitated protein. The supernatant was further diluted with 10 μL of 100 mM ammonium formate, pH 3. For HILIC analysis, the samples were diluted with 60 μL LCMS grade acetonitrile (ThermoFisher), whereas samples for C18 analysis were diluted with 60 μL water (GenPure ultrapure water system, Thermofisher). Each sample solution was transferred to 384-well microplate (Eppendorf) for LCMS analysis.

Frozen media samples were thawed on ice and 30 μl transferred to a 96-well microplate (Eppendorf) containing 30 μL of 100 mM ammonium formate, pH 3.0. The microplates were heat sealed, vortexed for 5 min at 750 rpm, and centrifuged at 2000×g for 10 min at room temperature. For HILIC analysis, 25 μL of sample was transferred to a new 96 well microplate containing 75 μL acetonitrile, whereas samples for C18 analysis were transferred to a new 96-well microplate containing 75 μL water (GenPure ultrapure water system, Thermofisher). Each sample solution was transferred to 384-well microplate (Eppendorf) for LCMS analysis.

For each batch, samples were randomized and matrix-matched reference quality controls and batch-specific pooled quality controls were included.

Semi-quantitative measurement of plasma polyamines was conducted on a Waters Acquity™ UPLC system with 2D column regeneration (I-class and H-class) coupled to a Xevo G2-XS quadrupole time-of-flight (qTOF) mass spectrometer. Chromatographic separation was performed using HILIC (Acquity™ UPLC BEH amide, 100 Å, 1.7 μm 2.1×100 mm) and C18 (Acquity™ UPLC HSS T3, 100 Å, 1.8 μm, 2.1×100 mm) columns at 45° C. Mass spectrometry data was acquired in sensitivity, positive and negative electrospray ionization modes. Acquisition was carried out with instrument auto-gain control to optimize sensitivity during sample acquisition; data processing was performed as previously described (Fahrmann 2018, Fahrmann 2019).

Procedure 4: Measurement of CA125 Levels

Automated immunoassay kits for determining the concentration of CA125 antigen were purchased from Roche Diagnostics USA (Indianapolis, Indiana).

Procedure 5: Cell Culture and Transfection

The SKOv3 serous carcinoma cell line was maintained in RPMI medium supplemented with 10% FBS. The identity of this line was confirmed by DNA fingerprinting via short tandem repeats at the time of mRNA and total protein lysate preparation using Promega PowerPlex 1.2 kit. Fingerprinting results were verified against reference fingerprints maintained by primary sources.

Small interfering RNA (siRNA) transfection experiments were performed using the following siRNAs (ThermoFisher): siControl (Silencer Select Negative Control #1), siMYC #1 and #3 (Sigma Aldrich Hs01_00222676 and Hs01_00222678). Cells were transfected at a final concentration of 20 nM siRNA using Lipofectamine RNAiMAX, according to the manufacturer's instructions. Cell lysates and conditioned media were collected 48 hours post transfection for RT-qPCR and metabolomics profiling, respectively.

Procedure 6: RT-qPCR Analysis

RNA was extracted using RNeasy Extraction Kit (Qiagen) according to the manufacturer's protocol. Complementary DNA samples were prepared by combining 10 μL of RNA (100 ng) with 0.8 μL 100 mM dNTPs, 1 μL 10× multiscribe reverse transcriptase, 1 μL of 10× reaction buffer, 2 μL random primers, 1 μL RNase inhibitor and 3.2 μL of ultrapure water (all reagents from Applied Biosciences). PCR cDNA preparation was performed using an Eppendorf Thermal Cycler. Cycling conditions were 25° C./10 min, 37° C./120 min, 85° C./5 min followed by returned to 4° C. TaqMan PCR was performed using universal TaqMan PCR master mix (ThermoFisher) and FAM™-labelled probes for MYC (Hs00153408_m1), ODC1 (Hs00159739_m1), SRM (Hs01027696_g1), and SMS (Hs019224834_u1) and VIC-™_labelled probes for GUSB (Hs_00939627_m1). PCR reactions were carried out using a BioRad CFX Connect RT System. Cycling conditions were 50° C./2 min, 95° C./10 min followed by 40 cycles at 95° C./15 sec to 60° C./1 min. Each sample was run in duplicate. Ct values for each gene were calculated and normalized to CT values for GUSB (ΔCT). The ΔΔCT values were then calculated by normalization to the ΔCT values for control.

Procedure 7: Gene Expression Data

Gene expression for polyamine metabolizing enzymes (PMEs) ornithine decarboxylase 1 (ODC1), adenosylmethionine decarboxylase 1 (AMD1), ornithine decarboxylase antizyme 1 (OAZ1), spermidine synthase (SRM), spermine synthase (SMS), spermine oxidase (SMOX), polyamine oxidase (PAOX), and spermidine/spermine N1-acetyltransferase 1 (SAT1) in 586 serous carcinomas and 8 normal ovarian tissues from The Cancer Genome Atlas (TCGA) ovarian cancer dataset was downloaded from Oncomine database [12] (https://www.oncomine.org/resource/login.html). Gene expression was derived using an Affymetrix Human Genome U133A array; values were log 2 median-centered.

Procedure 8: Statistical Analyses

Univariate analyses were conducted using the Kruskal Wallis test for comparisons with more than 2 groups; group specific differences were determined using Dunn's multiple comparison test and adjusted-p values were reported. For two-class comparisons, statistical significance was determined using Wilcoxon rank sum test. Statistical significance was determined at p-values<0.05. Receiver operating characteristic curves were generated using R. The 95% confidence intervals presented for individual performance of each biomarker were based on the bootstrap procedure in which re-sampling with replacement was done separately for the controls and the diseased 1000 bootstrap samples. To identify the optimal combination of markers amongst CA125 and 4 other polyamines, Lasso regression was implemented. Ten-fold cross-validation on the training dataset with AUC as the measurement of classification performance was incorporated to find the best tuning parameters (k). This parameter yielded CA125, DAS and N3AP as the best combination of biomarkers; a biomarker panel using CA125, DAS and N3AP was subsequently derived using a logistic regression model. Model building was based on a logistic regression model. The estimated AUC of the proposed metabolite panel was derived by using the empirical ROC estimator of the linear combination corresponding to the aforementioned model. McNemar's exact test were used to compare the performance of two distinct models at a given specificity. All statistical tests were two-sided unless specified otherwise.

Confusion matrices were utilized to describe the classification model of the 3-marker panel or CA125 alone at a 99% specificity cutoff. Rows of the matrix display the predicted classes (case or control) whereas columns represent the actual classes (case or control). To test whether 3-marker panel yielded statistically significant classifier improvement over CA125, the McNemar exact test was applied to the 2×2 contingency table wherein the first cell represents the number of patients that both markers predict correctly (a), second one represents the number of patients correctly identified by CA125 and misclassified by 3-marker panel (b), third one represents the number of patients misclassified by CA125 but correctly identified by 3-marker panel (c) and the last cell represents the number of patients misclassified by both markers (d). Therefore, the null and alternative hypothesize are as follows:

$$H_0: P_b = P_c$$

$$H_a: P_b < P_c$$

Herein, $P_i$ denotes the probability of occurrence in cell i. Exact binomial test was used to achieve p-value.

Figure 1A:
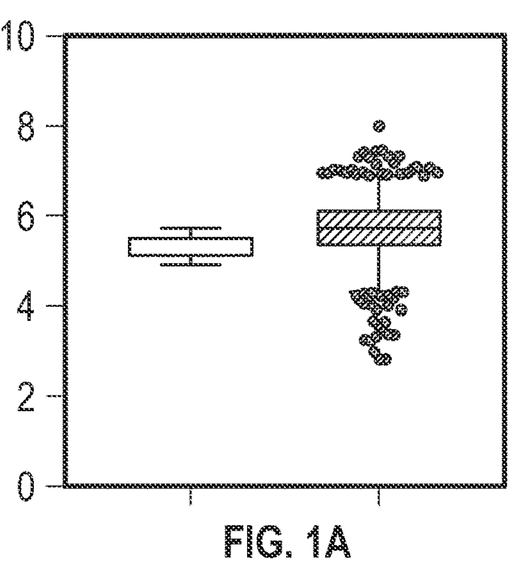
FIG. 1A-FIG. 1C depict regulation of polyamine metabolism by different polyamine-metabolizing enzymes in ovarian cancer by MYC.
Figure 1B:
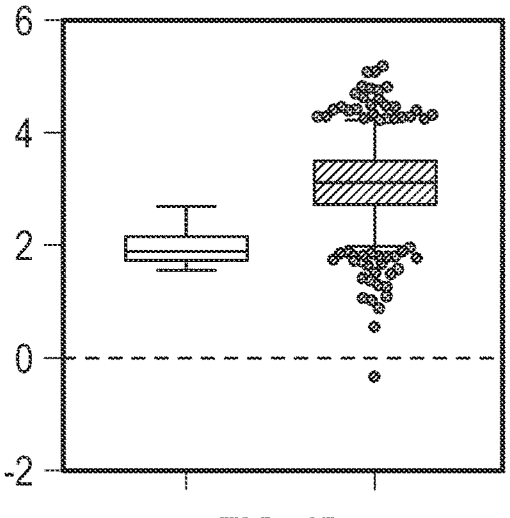
Figure 1C:
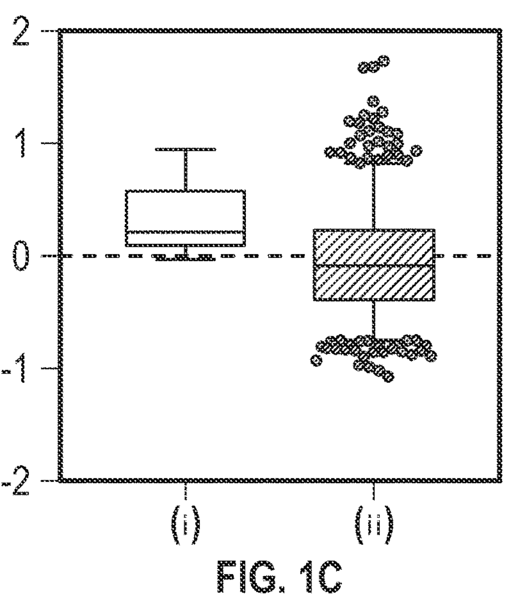

Example 1. Association Between MYC and Polyamine Metabolism in Ovarian Cancer To provide evidence that MYC regulates polyamine metabolism in the context of ovarian cancer, gene expression of polyamine metabolizing enzymes (PMEs) in ovarian serous carcinomas and normal ovarian tissue was evaluated using the TCGA-ovarian cancer transcriptomic dataset. Of the PMEs, gene expression levels of ornithine decarboxylase 1 (ODC1), a rate-limiting enzyme in polyamine metabolism, and spermine synthase (SMS) were statistically significantly elevated (1-sided Wilcoxon rank sum test p: 0.04, <0.0001, respectively) in ovarian serous carcinomas in comparison to normal ovarian tissue; whereas polyamine oxidase (PAOX), which catalyzes the oxidation of acetylated polyamines, was statistically significantly reduced (1-sided Wilcoxon rank sum test p: 0.01) (FIG. 1A-FIG. 1C). These findings implicate elevated polyamine metabolism in ovarian cancer.

Figure 2A:
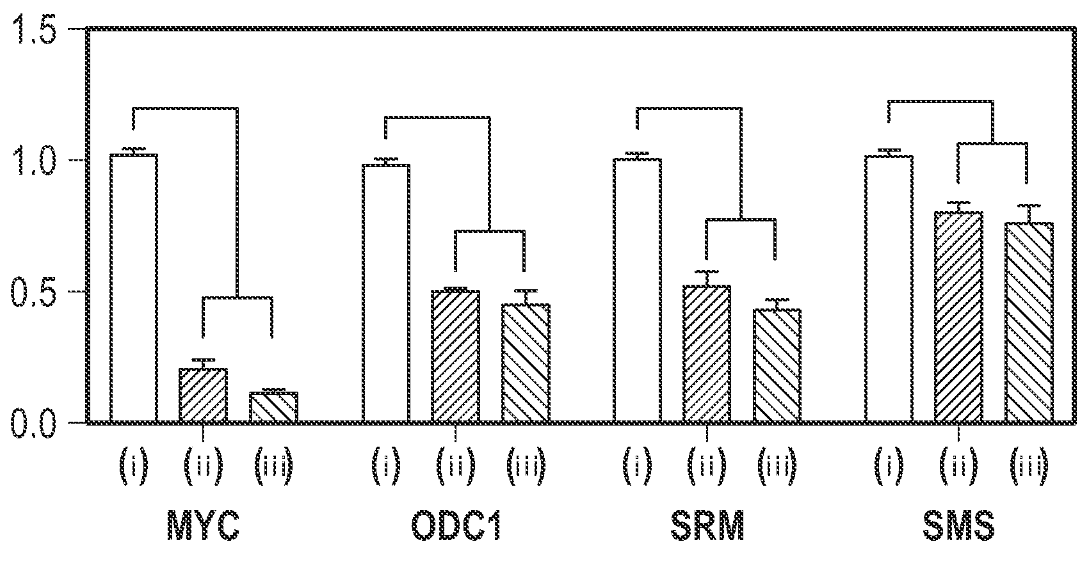
FIG. 2A and FIG. 2B depict polyamine metabolism in ovarian cancer by MYC.
Figure 2B:
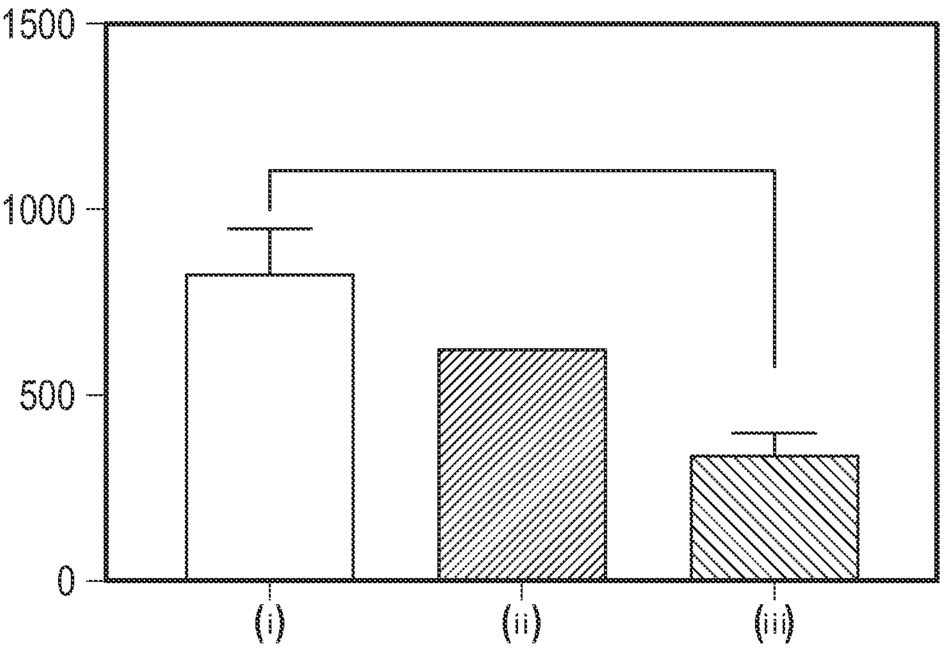

Next, siRNA-mediated knockdown of MYC was performed in the serous carcinoma cell line SKOv3, and gene expression of ODC1, SRM, and SMS was evaluated. Consistent with previous findings (Fahrmann 2019), siRNA-mediated knockdown of MYC resulted in statistically significantly reduced mRNA levels of ODC1, SRM and SMS (1-sided student t-tests p<0.001, <0.001, <0.001, respectively) (FIG. 2A). Further, levels of diacetylspermine (DAS) were statistically significantly reduced (2-sided student t-test p: 0.04) in conditioned media of SKOv3 ovarian cancer cells following siRNA-mediated knockdown of MYC (FIG. 2B). These findings substantiate the hypothesis that MYC regulates polyamine metabolism in ovarian cancer.

Example 2. Polyamine Levels in Plasma of Ovarian Cancer Patients and Model Development To determine whether a polyamine signature is associated with ovarian cancer, polyamine levels in plasma from Test Set #1 (Table 1) was screened using UPLC/MS. Several polyamines were quantified (Table 3).

TABLE 3

Measured polyamines

| Metabolite | Adduct | m/z | retention time, min | assay† |
|---|---|---|---|---|
| AcSpmd | $[M + H]^+$ | 188.1751 | 385 | P_HA |
| DiAcSpmd | $[M + H]^+$ | 230.1858 | 3.11 | P_HA |
| DAS | $[M + H]^+$ | 287.2418 | 3.72 | P_HA |
| N3AP | $[M + H]^+$ | 185.1277 | 2.12 | P_CA |

Figures 3A, 3B, 3C:
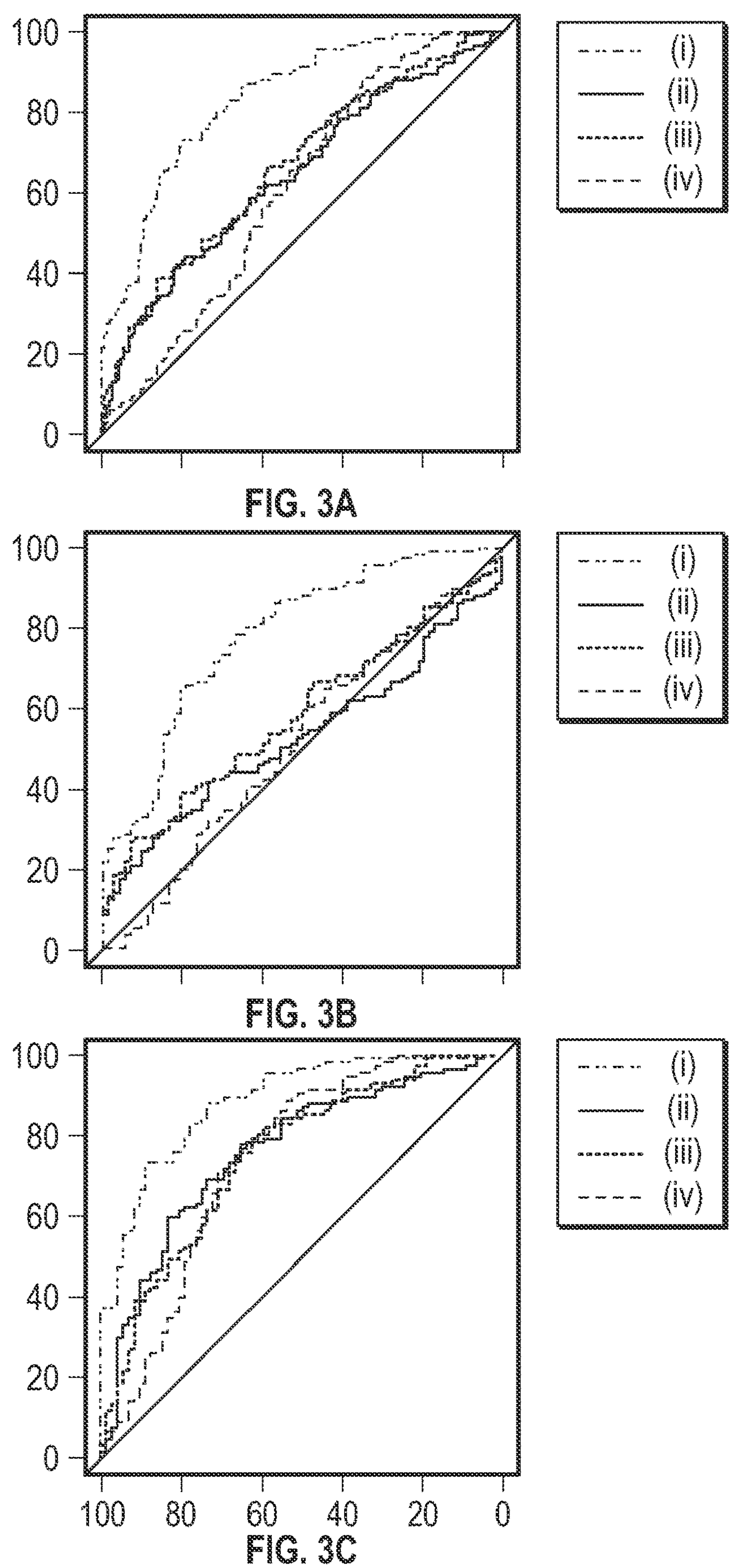
FIG. 3A-FIG. 3C depict classification performances of individual plasma polyamines (i) DAS (ii) AcSpmd (iii) N3AP (iv) DiAcSpmd against Test Set #1. Area under the curve (AUC) of DAS for delineating all cases (n=116) from all controls (n=143) (FIG. 3A), patients with benign pelvic masses (n=72) (FIG. 3B), and healthy controls (n=71) (FIG. 3C). Horizontal axis=specificity (%); vertical axis=sensitivity (%).
Figures 4A, 4B, 4C, 4D:
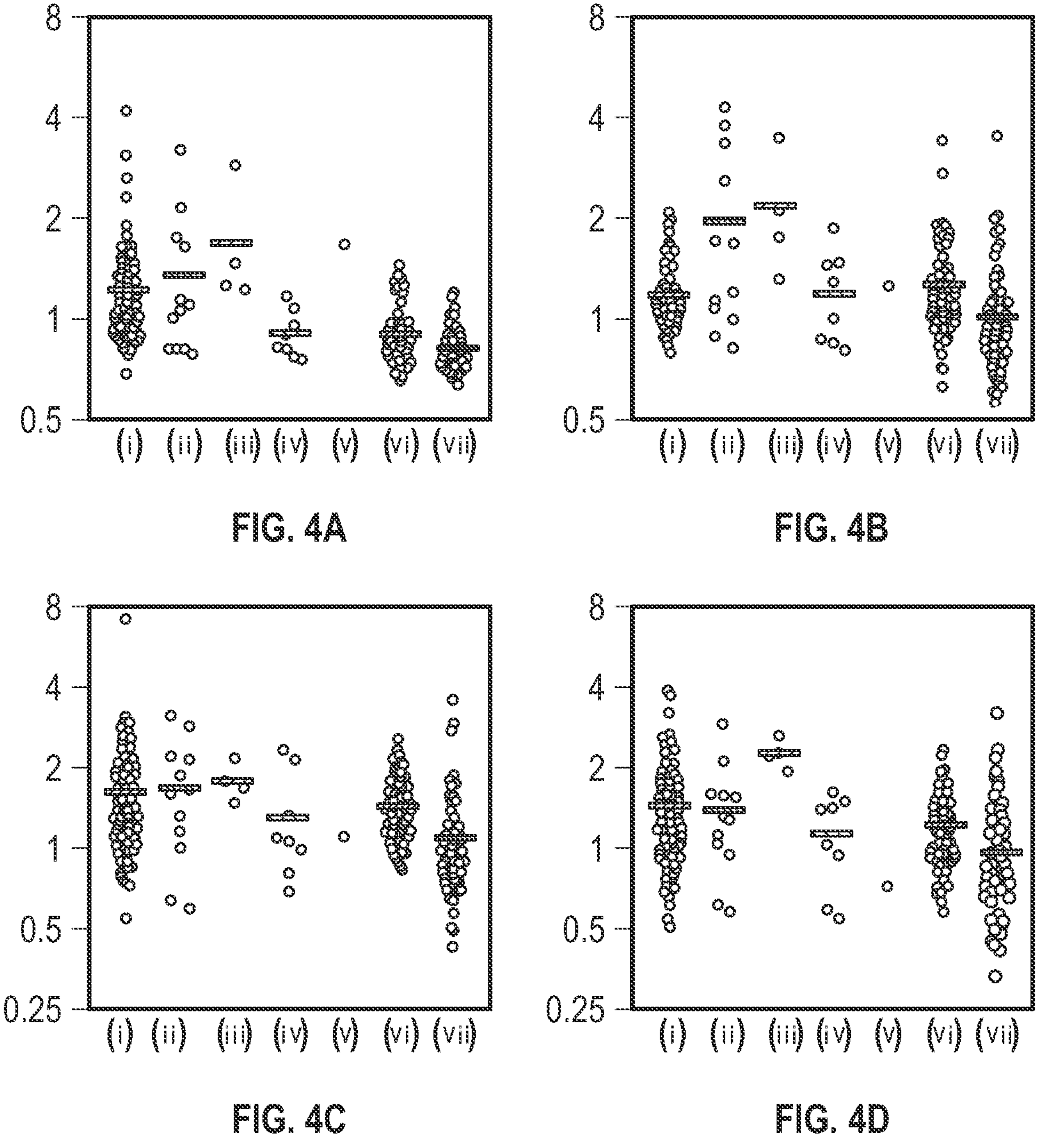
FIG. 4A-FIG. 4D depict plasma levels of polyamines DAS (FIG. 4A), DiAcSpmd (FIG. 4B), AcSpmd (FIG. 4C), and N3AP (FIG. 4D), in cases stratified by histology and controls against Test Set #1. (i) Serous (n=91) (ii) endometrioid (n=12) (iii) mucinous (n=4) (iv) clear cell carcinoma (n=8) (v) other (n=1) (vi) benign ovarian cysts (n=72) (vii) healthy controls (n=71). Vertical axis=standardized values.

†P: Electrospray ionization positive acquisition mode; HA: HLIC Acidic; CA: C18 Acidic AUCs of individual polyamines for distinguishing ovarian cancer from all controls ranged from 0.61-0.83 (Table 4(a)(i)). Of the measured polyamines, DAS exhibited the highest classification performance for distinguishing ovarian cancer cases from patients with benign pelvic masses (AUC: 0.78, Table 4(a)(ii); FIG. 3B) or from healthy controls (AUC: 0.88, Table 4(a)(iii); FIG. 3C).

TABLE 4

Classification performances of plasma polyamines in distinguishing ovarian cancer cases from controls against Test Set #1.

| Metabolite | AUC | 95% CI | p-value† | Sens @ 95% Spec | Spec @ 95% Sens |
|---|---|---|---|---|---|
| (a) all ovarian cancer cases (n = 116) (i) vs. all controls (n = 143) | | | | | |
| DAS | 0.83 | 0.78-0.88 | <0.0001 | 32.8 | 46.9 |
| DiAcSpmd | 0.61 | 0.54-0.68 | 0.002 | 7.8 | 21.0 |
| AcSpmd | 0.64 | 0.58-0.71 | <0.0001 | 19.0 | 9.8 |
| N3AP | 0.66 | 0.60-0.73 | <0.0001 | 19.0 | 11.2 |
| (ii) vs. subjects with benign cysts (n = 72) | | | | | |
| DAS | 0.78 | 0.72-0.85 | <0.0001 | 28.4 | 34.7 |
| DiAcSpmd | 0.52 | 0.43-0.60 | 0.73 | 0 | 2.8 |
| AcSpmd | 0.53 | 0.45-0.61 | 0.50 | 17.2 | 0 |
| N3AP | 0.58 | 0.50-0.66 | 0.06 | 19.0 | 1.4 |
| (iii) vs. healthy controls (n = 71) | | | | | |
| DAS | 0.88 | 0.84-0.93 | <0.0001 | 47.4 | 59.2 |
| DiAcSpmd | 0.74 | 0.66-0.82 | <0.0001 | 8.6 | 35.2 |
| AcSpmd | 0.76 | 0.69-0.83 | <0.0001 | 29.3 | 19.7 |
| N3AP | 0.75 | 0.67-0.82 | <0.0001 | 18.1 | 21.1 |
| (b) early stage ovarian cancer cases (n = 41) (i) vs. all controls (n = 143) | | | | | |
| DAS | 0.76 | 0.68-0.85 | <0.0001 | 29.3 | 32.9 |
| DiAcSpmd | 0.67 | 0.57-0.77 | 0.001 | 19.5 | 18.2 |
| AcSpmd | 0.60 | 0.49-0.71 | 0.06 | 24.4 | 2.8 |
| N3AP | 0.63 | 0.53-0.73 | 0.01 | 22.0 | 11.2 |
| (ii) vs. subjects with benign cysts (n = 72) | | | | | |
| DAS | 0.70 | 0.60-0.81 | 0.0003 | 24.4 | 22.2 |
| DiAcSpmd | 0.58 | 0.46-0.70 | 0.17 | 17.1 | 5.6 |
| AcSpmd | 0.50 | 0.38-0.63 | 0.98 | 22.0 | 0 |
| N3AP | 0.55 | 0.43-0.67 | 0.38 | 22.0 | 1.4 |
| (iii) vs. healthy controls (n = 71) | | | | | |
| DAS | 0.82 | 0.74-0.90 | <0.0001 | 43.9 | 43.7 |
| DiAcSpmd | 0.76 | 0.67-0.85 | <0.0001 | 22.0 | 31.0 |
| AcSpmd | 0.70 | 0.59-0.81 | 0.0005 | 29.3 | 5.6 |
| N3AP | 0.72 | 0.62-0.82 | 0.0001 | 19.5 | 21.1 |
| (c) late stage ovarian cancer cases (n = 75) (i) vs. all controls (n = 143) | | | | | |
| DAS | 0.87 | 0.83-0.92 | <0.0001 | 34.7 | 65.0 |
| DiAcSpmd | 0.58 | 0.51-0.65 | 0.055 | 1.3 | 31.5 |
| AcSpmd | 0.67 | 0.59-0.74 | <0.0001 | 16.0 | 20.3 |
| N3AP | 0.68 | 0.61-0.76 | <0.0001 | 17.3 | 18.9 |
| (ii) vs. subjects with benign cysts (n = 72) | | | | | |
| DAS | 0.83 | 0.76-0.89 | <0.0001 | 30.7 | 56.9 |
| DiAcSpmd | 0.57 | 0.47-0.66 | 0.17 | 0 | 18.1 |
| AcSpmd | 0.55 | 0.45-0.64 | 0.33 | 16.0 | 2.8 |
| N3AP | 0.60 | 0.51-0.69 | 0.035 | 17.3 | 5.6 |
| (iii) vs. healthy controls (n = 71) | | | | | |
| DAS | 0.92 | 0.88-0.96 | <0.0001 | 49.3 | 73.2 |
| DiAcSpmd | 0.73 | 0.64-0.82 | <0.0001 | 1.3 | 50.7 |
| AcSpmd | 0.79 | 0.72-0.87 | <0.0001 | 29.3 | 38.0 |
| N3AP | 0.76 | 0.69-0.84 | <0.0001 | 17.3 | 32.4 |

AUCs of DAS for distinguishing all serous cases from all controls, or subjects with benign pelvic masses or healthy controls were 0.85, 0.80 and 0.90, respectively (Table 5(a)(i)(ii)(iii)). When considering only early stage serous cases, DAS yielded AUCs of 0.76, 0.70 and 0.81 in comparison to all controls, subjects with benign pelvic masses or healthy controls,

TABLE 5

Classification performance of plasma polyamines in distinguishing serous cases from controls in the Test Set #1.

| Metabolite | AUC | 95% CI | p-value† | Sens @ 95% Spec | Spec @ 95% Sens |
|---|---|---|---|---|---|
| (a) all serous cases (n = 91) | | | | | |
| (i) vs. all controls (n = 143) | | | | | |
| DAS | 0.85 | 0.80-0.90 | <0.0001 | 33.0 | 58.0 |
| DiAcSpmd | 0.59 | 0.52-0.66 | 0.022 | 3.3 | 25.2 |
| AcSpmd | 0.65 | 0.58-0.72 | 0.0001 | 16.5 | 11.9 |
| N3AP | 0.67 | 0.60-0.74 | <0.0001 | 17.6 | 18.9 |
| (ii) vs. subjects with benign cysts (n = 72) | | | | | |
| DAS | 0.80 | 0.74-0.87 | <0.0001 | 28.6 | 47.2 |
| DiAcSpmd | 0.55 | 0.46-0.64 | 0.28 | 0 | 9.7 |
| AcSpmd | 0.53 | 0.44-0.62 | 0.50 | 16.5 | 0 |
| N3AP | 0.58 | 0.50-0.67 | 0.065 | 17.6 | 5.6 |
| (iii) vs. healthy controls (n = 71) | | | | | |
| DAS | 0.90 | 0.85-0.95 | <0.0001 | 47.3 | 69.0 |
| DiAcSpmd | 0.73 | 0.64-0.81 | <0.0001 | 3.3 | 39.4 |
| AcSpmd | 0.77 | 0.69-0.84 | <0.0001 | 29.7 | 23.9 |
| N3AP | 0.75 | 0.68-0.83 | <0.0001 | 17.6 | 32.4 |
| (b) early stage serous cases (n = 16) | | | | | |
| (i) vs. all controls (n = 143) | | | | | |
| DAS | 0.76 | 0.63-0.88 | 0.0008 | 25.0 | 4.9 |
| DiAcSpmd | 0.63 | 0.49-0.77 | 0.082 | 12.5 | 15.4 |
| AcSpmd | 0.56 | 0.37-0.74 | 0.46 | 18.8 | 2.1 |
| N3AP | 0.60 | 0.46-0.75 | 0.18 | 18.8 | 9.1 |
| (ii) vs. subjects with benign cysts (n = 72) | | | | | |
| DAS | 0.70 | 0.56-0.84 | 0.013 | 18.8 | 5.6 |
| DiAcSpmd | 0.47 | 0.30-0.64 | 0.74 | 0 | 2.8 |
| AcSpmd | 0.54 | 0.34-0.75 | 0.58 | 31.3 | 0 |
| N3AP | 0.51 | 0.34-0.68 | 0.94 | 18.8 | 0 |
| (iii) vs. healthy controls (n = 71) | | | | | |
| DAS | 0.81 | 0.69-0.94 | 0.0001 | 37.5 | 4.2 |
| DiAcSpmd | 0.74 | 0.62-0.87 | 0.003 | 12.5 | 25.4 |
| AcSpmd | 0.66 | 0.49-0.83 | 0.049 | 31.3 | 4.2 |
| N3AP | 0.70 | 0.56-0.84 | 0.013 | 18.8 | 18.3 |
| (c) late stage serous cases | | | | | |
| (i) vs. all controls (n = 143) | | | | | |
| DAS | 0.87 | 0.83-0.92 | <0.0001 | 34.7 | 65.0 |
| DiAcSpmd | 0.58 | 0.51-0.65 | 0.055 | 1.3 | 31.5 |
| AcSpmd | 0.67 | 0.59-0.74 | <0.0001 | 16.0 | 20.3 |
| N3AP | 0.68 | 0.61-0.76 | <0.0001 | 17.3 | 18.9 |
| (ii) vs. subjects with benign cysts (n = 72) | | | | | |
| DAS | 0.83 | 0.76-0.89 | <0.0001 | 30.7 | 56.9 |
| DiAcSpmd | 0.57 | 0.47-0.66 | 0.17 | 0 | 18.1 |
| AcSpmd | 0.55 | 0.45-0.64 | 0.33 | 16.0 | 2.8 |
| N3AP | 0.60 | 0.51-0.69 | 0.035 | 17.3 | 5.6 |
| (iii) vs. healthy controls (n = 71) | | | | | |
| DAS | 0.92 | 0.88-0.96 | <0.0001 | 49.3 | 73.2 |
| DiAcSpmd | 0.73 | 0.64-0.82 | <0.0001 | 1.3 | 50.7 |
| AcSpmd | 0.79 | 0.72-0.87 | <0.0001 | 29.3 | 38.0 |
| N3AP | 0.76 | 0.69-0.84 | <0.0001 | 17.3 | 32.4 |

AUCs of DAS for distinguishing non-serous ovarian cancer cases from all controls, or subjects with benign pelvic masses or healthy controls were 0.77, 0.71, and 0.83, respectively (Table 6(i)(ii)(iii); FIG. 4A-FIG. 4D).

TABLE 6

Classification performance of plasma polyamines in distinguishing non-serous cases from controls in the Test Set #1.

| Metabolite | AUC | 95% CI | p-value† | Sens @ 95% Spec | Spec @ 95% Sens |
|---|---|---|---|---|---|
| (i) vs. all controls (n = 143) | | | | | |
| DAS | 0.77 | 0.66-0.87 | <0.0001 | 32.0 | 32.9 |
| DiAcSpmd | 0.69 | 0.57-0.81 | 0.002 | 24.0 | 18.2 |
| AcSpmd | 0.62 | 0.49-0.76 | 0.050 | 28.0 | 2.8 |
| N3AP | 0.65 | 0.52-0.78 | 0.016 | 24.0 | 11.2 |
| (ii) vs. subjects with benign disease (n = 72) | | | | | |
| DAS | 0.71 | 0.58-0.83 | 0.002 | 28.0 | 22.2 |
| DiAcSpmd | 0.61 | 0.46-0.76 | 0.098 | 24.0 | 5.6 |
| AcSpmd | 0.53 | 0.37-0.68 | 0.71 | 20.0 | 0 |
| N3AP | 0.58 | 0.43-0.73 | 0.25 | 24.0 | 1.4 |
| (iii) vs. healthy controls (n = 71) | | | | | |
| DAS | 0.83 | 0.73-0.92 | <0.0001 | 48.0 | 43.7 |
| DiAcSpmd | 0.77 | 0.67-0.88 | <0.0001 | 28.0 | 31.0 |
| AcSpmd | 0.72 | 0.59-0.85 | 0.001 | 28.0 | 5.6 |
| N3AP | 0.73 | 0.61-0.85 | 0.0008 | 20.0 | 21.1 |

Example 3. Assessment of 3-Marker Panel

Figures 5A, 5B:
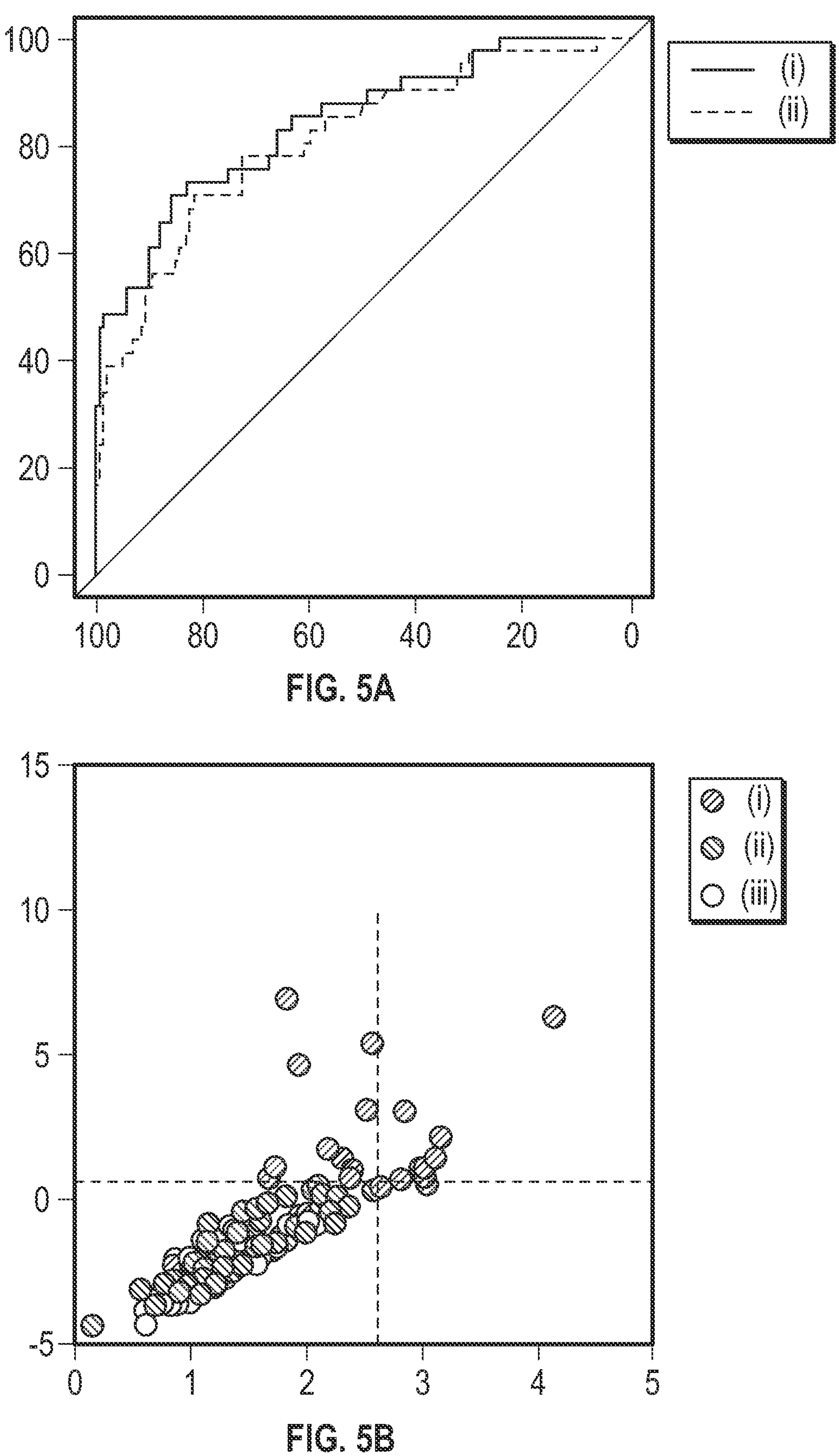
FIG. 5A-FIG. 5B depict classification performance of the 3-marker panel and CA125 against Test Set #1.

Using logistic regression models, the relative performance of the combination of polyamines plus CA125, compared to CA125 alone, in differentiating early stage ovarian cancer cases from controls (healthy subjects+subjects with benign pelvic masses) was next assessed. Logistic regression with variable selection methods (Lasso L1 penalty with AUC as the loss function for cross-validation) identified the combination of plasma DAS+N3AP+CA125 as the best panel with an AUC point estimate of 0.84 (95% C.I.: 0.77-0.92), compared to an AUC point estimate of 0.81 (95% C.I.: 0.73-0.89) for CA125 (FIG. 5A).

Therefore, the sensitivity of the 3-marker panel (DAS+N3AP+CA125) at corresponding specificities of 99%, 98.5% and 97%, in comparison to CA125 alone, was next evaluated (Table 7). Compared to CA125 alone, the 3-marker panel yielded statistically significantly improved sensitivity at 99% and 98.5% specificity.

TABLE 7

Sensitivity of the 3-marker panel and CA125 alone at various specificity cutoff values against Test Set #1.

| Cutoffs | DAS + N3AP + CA125 | CA125 | McNemar Exact Test 1-sided p-value |
|---|---|---|---|
| Sensitivity @ 99% Specificity | 46.3 | 24.3 | 0.006 |
| Sensitivity @ 98.5% Specificity | 48.8 | 34.1 | 0.035 |
| Sensitivity @ 97% Specificity | 48.8 | 39.2 | 0.17 |

A confusion matrix describing the performance of the classification model corresponding to the 3-marker panel and CA125 alone at 99% specificity illustrates that the 3-marker panel correctly identified 19 out of 41 early stage ovarian cancer cases (46.3% sensitivity) whereas CA125 alone correctly identified 10 out of 41 early stage ovarian cancer cases (24.3% sensitivity) (1-sided McNemar exact test p: 0.006) (Table 8; FIG. 5B).

TABLE 8

Confusion matrix: Test Set 1

| | DAS + N3AP + CA125 | | |
|---|---|---|---|
| | 1 Case | 0 Control | |
| 1 Case | 19 | 1 | 20 |
| 0 Control | 22 | 141 | 163 |
| | 41 | 142 | 183 |
| | **CA125 Only** | | |
| | 1 Case | 0 Control | |
| 1 Case | 10 | 1 | 11 |
| 0 Control | 31 | 141 | 172 |
| | 41 | 142 | 183 |

Example 4. Model Validation in an Independent Cohort of Early Stage Ovarian Cancer Patients Further validation of the polyamine metabolites individually and the fixed 3-marker panel consisting of DAS+N3AP+CA125 was performed on validation Set #2 (Table 2). AUCs for individual polyamine metabolites ranged from 0.57-0.84, with the highest AUC point for plasma DAS (Table 9(a); FIG. 6A). Classification performance of plasma DAS in distinguishing serous (n=28) and non-serous cases (n=33) from healthy controls was 0.84 and 0.84, respectively (Table 9(b)(c); FIG. 7A-FIG. 7D).

TABLE 9

Classification performance of plasma polyamines in distinguishing serous or non-serous cases from controls against validation Set #2

| Metabolite | AUC | 95% CI | p-value† | Sens @ 95% Spec | Spec @ 95% Sens |
|---|---|---|---|---|---|
| (a) all cases (n = 61) vs. controls (n = 71) | | | | | |
| DAS | 0.84 | 0.77-0.91 | <0.0001 | 52.5 | 33.8 |
| DiAcSpmd | 0.57 | 0.47-0.67 | 0.18 | 13.1 | 1.4 |
| AcSpmd | 0.67 | 0.57-0.77 | 0.0009 | 27.9 | 2.8 |
| N3AP | 0.59 | 0.49-0.69 | 0.082 | 18.0 | 4.2 |
| (b) serous cases (n = 28) vs. controls (n = 71) | | | | | |
| DAS | 0.84 | 0.75-0.93 | <0.0001 | 46.4 | 33.8 |
| DiAcSpmd | 0.56 | 0.42-0.70 | 0.33 | 10.7 | 0 |
| AcSpmd | 0.64 | 0.50-0.78 | 0.028 | 25.0 | 2.8 |
| N3AP | 0.58 | 0.44-0.72 | 0.21 | 17.9 | 4.2 |
| (c) non-serous cases (n = 33) vs. controls (n = 71) | | | | | |
| DAS | 0.84 | 0.75-0.92 | <0.0001 | 57.6 | 23.9 |
| DiAcSpmd | 0.57 | 0.44-0.70 | 0.25 | 15.2 | 1.4 |
| AcSpmd | 0.69 | 0.57-0.81 | 0.002 | 30.3 | 2.8 |
| N3AP | 0.59 | 0.46-0.72 | 0.12 | 18.2 | 2.8 |

Sensitivity of the 3-marker panel using fixed covariant-coefficients derived from Test Set #1 at corresponding specificities of >99%, 98.5% and 97% for validation Set #2 were 73.7, 78.6 and 83.6, respectively (Table 10). Compared to CA125 alone, the 3-marker panel yielded statistically significantly improved sensitivity at >99% specificity.

TABLE 10

Sensitivity of the 3-marker panel and CA125 alone at various specificity cutoff values against validation Set #2.

| Cutoffs | DAS + N3AP + CA125 | CA125 | McNemar Exact Test 1-sided p-value |
|---|---|---|---|
| Sensitivity @ 99% Specificity | 73.7 | 62.2 | 0.019 |
| Sensitivity @ 98.5% Specificity | 78.6 | 81.9 | 0.37 |
| Sensitivity @ 97% Specificity | 83.6 | 86.8 | 0.38 |

A confusion matrix describing the performance of the classification model corresponding to the 3-marker panel and CA125 alone at >99% specificity shows that the 3-marker panel correctly identified 45 out of 61 early stage ovarian cancer cases whereas CA125 alone correctly identified 38 out of 61 early stage ovarian cancer cases which corresponds to capturing 30.4% of cases missed by CA125 alone (Table 11; FIG. 6B).

TABLE 11

Confusion matrix: validation Set #2

| | DAS + N3AP + CA125 | | |
|---|---|---|---|
| | 1 Case | 0 Control | |
| 1 Case | 45 | 0 | 45 |
| 0 Control | 16 | 71 | 87 |
| | 61 | 71 | 132 |
| | **CA125 Only** | | |
| | 1 Case | 0 Control | |
| 1 Case | 38 | 0 | 38 |
| 0 Control | 23 | 71 | 94 |
| | 61 | 71 | 132 |

A CA125 cutoff value of 35 U/mL is considered upper limit of 'normal.' In validation Set #2, a cutoff value of 35 U/mL captured 53 out of 61 cases (86.9% sensitivity) with 2 false-positives (97.2% specificity). If considering cases 'negative' for CA125 (defined as <35 U/mL), the fixed 3-marker panel identifies an additional 2 of the 8 early stage cases (25.0% sensitivity) without any additional false-positives (FIG. 8). Notably, these 2 additional cases identified by the 3-marker panel were stage I high-grade serous carcinomas.

Example 5: Specificity and Sensitivity in the Range of Regression Model Diagnostic Scores In one example, a patient being screened for ovarian cancer-based on the three-biomarker panel disclosed herein—has a blood sample drawn (or other fluid or tissue biopsy) and assayed by ELISA (or other assay) to quantitate the levels of DAS, N3AP, and CA125 in the patient. Normalized values for at least these biomarkers that take into account the specific assay used could be, for example, DAS=5.57 ng/mL; N3AP=1.35; and CA125=86.7. For DAS and N3AP, semiquantitiave values are reported as ratios relative to the median of historical quality control reference samples run with every analytical batch for the given analyte. For CA125, raw values are log 10 transformed. When analyzed using the following regression model:

$$\text{logit}(p)=-7.0619+1.8065\times\log \text{CA125}+2.3582\times\text{DAS}+0.5139\times\text{N3AP}$$

the above patient would have a combined score of 10.27. In view of the preferred cutoff for consideration of both specificity and sensitivity (Table 12), a patient with such a combined score would have ovarian cancer with near certainty and consequently be directed for follow-up testing and treatment for ovarian cancer using other modalities discussed herein and known to those of skill in the art. Using the regression model described herein, the more positive the combined ovarian cancer-predictive score, the more certainty the patient has ovarian cancer. Conversely, the more negative the combined ovarian cancer-predictive score, the more certainty the patient does not have ovarian cancer.

It will be appreciated by those of ordinary skill in the art that different methods or assays of biomarker detection, quantitation, and analysis, which can include using different reagents, will produce different results which may require modification of the regression model. In particular, different assays can produce results expressed, for example, in different units. Further, duplicate reactions in duplicate assays of the same samples can also produce different raw results. However, it is the combined detection, quantitation, and analysis of at least the three biomarkers, DAS, N3AP, and CA125, that, when incorporated into a regression model as disclosed herein, produce a definitive diagnosis of ovarian cancer.

A range in the results reported for each particular assay used to detect, quantify, and analyze the four biomarkers will have a range in the resulting ovarian cancer-predictive score that depends, in part, on the degree of sensitivity or specificity. The regression model used to generate the ovarian cancer-predictive score can dependent on the specific assays utilized to test the markers. As understood by those of skill in the art, different assays can target different epitopes of the four biomarkers or have different affinities and sensitivities. As such, the regression model algorithm used to generate the ovarian cancer-predictive score can be modified to take these assay variations into consideration.

Measured concentrations are used to calculate a biomarker score based on a logistic regression model. Table 12 illustrates the sensitivity, specificity and corresponding youden index at different cutoff points of the biomarker panel-based (N3AP, DAS, and CA125) scores for distinguishing early stage OvCa cases from healthy controls in the Test Set #2 (Validation Set).

TABLE 12

Sensitivity and specificity at different cutoffs of the biomarker panel-based) scores in the combination validation set.

| Cutoff | Specificty | Sensitivity | Youden |
|---|---|---|---|
| −3.89723 | 0.014085 | 1 | 0.014085 |
| −3.73886 | 0.028169 | 1 | 0.028169 |
| −3.72305 | 0.042254 | 1 | 0.042254 |
| −3.67017 | 0.056338 | 1 | 0.056338 |
| −3.60971 | 0.070423 | 1 | 0.070423 |
| −3.58379 | 0.084507 | 1 | 0.084507 |
| −3.55334 | 0.098592 | 1 | 0.098592 |
| −3.53452 | 0.112676 | 1 | 0.112676 |
| −3.51564 | 0.126761 | 1 | 0.126761 |
| −3.4814 | 0.140845 | 1 | 0.140845 |
| −3.44966 | 0.15493 | 1 | 0.15493 |
| −3.43298 | 0.169014 | 1 | 0.169014 |
| −3.39368 | 0.183099 | 1 | 0.183099 |
| −3.35388 | 0.197183 | 1 | 0.197183 |
| −3.34452 | 0.211268 | 1 | 0.211268 |
| −3.33973 | 0.225352 | 1 | 0.225352 |
| −3.32507 | 0.239437 | 1 | 0.239437 |
| −3.30088 | 0.253521 | 1 | 0.253521 |
| −3.28902 | 0.253521 | 0.983607 | 0.237128 |
| −3.26711 | 0.267606 | 0.983607 | 0.251212 |
| −3.24509 | 0.28169 | 0.983607 | 0.265297 |
| −3.23796 | 0.295775 | 0.983607 | 0.279381 |
| −3.22115 | 0.309859 | 0.983607 | 0.293466 |
| −3.20009 | 0.323944 | 0.983607 | 0.30755 |
| −3.18913 | 0.323944 | 0.967213 | 0.291157 |
| −3.18345 | 0.338028 | 0.967213 | 0.305241 |
| −3.16976 | 0.352113 | 0.967213 | 0.319326 |
| −3.15012 | 0.366197 | 0.967213 | 0.33341 |
| −3.10757 | 0.380282 | 0.967213 | 0.347495 |
| −3.06859 | 0.394366 | 0.967213 | 0.361579 |
| −3.05543 | 0.408451 | 0.967213 | 0.375664 |
| −3.04727 | 0.422535 | 0.967213 | 0.389748 |
| −3.04536 | 0.43662 | 0.967213 | 0.403833 |
| −3.02052 | 0.450704 | 0.967213 | 0.417917 |
| −2.99146 | 0.464789 | 0.967213 | 0.432002 |
| −2.96315 | 0.478873 | 0.967213 | 0.446086 |
| −2.93488 | 0.478873 | 0.95082 | 0.429693 |
| −2.92994 | 0.492958 | 0.95082 | 0.443777 |
| −2.92939 | 0.507042 | 0.95082 | 0.457862 |
| −2.92652 | 0.521127 | 0.95082 | 0.471946 |
| −2.92184 | 0.535211 | 0.95082 | 0.486031 |
| −2.89301 | 0.549296 | 0.95082 | 0.500115 |
| −2.86133 | 0.56338 | 0.95082 | 0.5142 |
| −2.82242 | 0.577465 | 0.95082 | 0.528284 |
| −2.78755 | 0.591549 | 0.95082 | 0.542369 |
| −2.77344 | 0.605634 | 0.95082 | 0.556453 |
| −2.75971 | 0.619718 | 0.95082 | 0.570538 |
| −2.74528 | 0.633803 | 0.95082 | 0.584622 |
| −2.70105 | 0.647887 | 0.95082 | 0.598707 |
| −2.60977 | 0.661972 | 0.95082 | 0.612792 |
| −2.51448 | 0.676056 | 0.95082 | 0.626876 |
| −2.46893 | 0.690141 | 0.95082 | 0.640961 |
| −2.44219 | 0.704225 | 0.95082 | 0.655045 |
| −2.4246 | 0.71831 | 0.95082 | 0.66913 |
| −2.41206 | 0.71831 | 0.934426 | 0.652736 |
| −2.39 | 0.732394 | 0.934426 | 0.666821 |
| −2.36187 | 0.746479 | 0.934426 | 0.680905 |
| −2.33047 | 0.760563 | 0.934426 | 0.69499 |
| −2.31386 | 0.774648 | 0.934426 | 0.709074 |
| −2.2902 | 0.788732 | 0.934426 | 0.723159 |
| −2.26081 | 0.802817 | 0.934426 | 0.737243 |
| −2.24895 | 0.816901 | 0.934426 | 0.751328 |
| −2.23933 | 0.830986 | 0.934426 | 0.765412 |
| −2.1757 | 0.84507 | 0.934426 | 0.779497 |
| −2.10826 | 0.859155 | 0.934426 | 0.793581 |
| −2.08266 | 0.859155 | 0.918033 | 0.777188 |
| −2.04976 | 0.859155 | 0.901639 | 0.760794 |
| −2.02218 | 0.873239 | 0.901639 | 0.774879 |
| −1.99162 | 0.887324 | 0.901639 | 0.788963 |
| −1.95921 | 0.901408 | 0.901639 | 0.803048 |
| −1.93346 | 0.915493 | 0.901639 | 0.817132 |
| −1.87265 | 0.915493 | 0.885246 | 0.800739 |
| −1.79226 | 0.915493 | 0.868852 | 0.784345 |
| −1.7543 | 0.915493 | 0.852459 | 0.767952 |
| −1.74158 | 0.915493 | 0.836066 | 0.751559 |
| −1.73331 | 0.929577 | 0.836066 | 0.765643 |
| −1.69737 | 0.943662 | 0.836066 | 0.779728 |
| −1.63006 | 0.957746 | 0.836066 | 0.793812 |
| −1.5924 | 0.971831 | 0.836066 | 0.807897 |
| −1.54697 | 0.971831 | 0.819672 | 0.791503 |
| −1.50204 | 0.971831 | 0.803279 | 0.77511 |
| −1.49678 | 0.971831 | 0.786885 | 0.758716 |
| −1.49419 | 0.985915 | 0.786885 | 0.772801 |
| −1.46244 | 0.985915 | 0.770492 | 0.756407 |
| −1.41012 | 0.985915 | 0.754098 | 0.740014 |
| −1.32142 | 0.985915 | 0.737705 | 0.72362 |
| −1.24268 | 1 | 0.737705 | 0.737705 |
| −1.22354 | 1 | 0.721311 | 0.721311 |
| −1.08778 | 1 | 0.704918 | 0.704918 |
| −0.94855 | 1 | 0.688525 | 0.688525 |
| −0.93817 | 1 | 0.672131 | 0.672131 |

TABLE 12-continued

Sensitivity and specificity at different cutoffs of the biomarker panel-based) scores in the combination validation set.

| Cutoff | Specificty | Sensitivity | Youden |
|---|---|---|---|
| −0.93233 | 1 | 0.655738 | 0.655738 |
| −0.89965 | 1 | 0.639344 | 0.639344 |
| −0.8418 | 1 | 0.622951 | 0.622951 |
| −0.80743 | 1 | 0.606557 | 0.606557 |
| −0.77246 | 1 | 0.590164 | 0.590164 |
| −0.70337 | 1 | 0.57377 | 0.57377 |
| −0.54372 | 1 | 0.557377 | 0.557377 |
| −0.36713 | 1 | 0.540984 | 0.540984 |
| −0.20187 | 1 | 0.52459 | 0.52459 |
| 0.098919 | 1 | 0.508197 | 0.508197 |
| 0.333439 | 1 | 0.491803 | 0.491803 |
| 0.412165 | 1 | 0.47541 | 0.47541 |
| 0.494346 | 1 | 0.459016 | 0.459016 |
| 0.569211 | 1 | 0.442623 | 0.442623 |
| 0.693978 | 1 | 0.42623 | 0.42623 |
| 0.804154 | 1 | 0.409836 | 0.409836 |
| 0.955443 | 1 | 0.393443 | 0.393443 |
| 1.231879 | 1 | 0.377049 | 0.377049 |
| 1.429552 | 1 | 0.360656 | 0.360656 |
| 1.550801 | 1 | 0.344262 | 0.344262 |
| 1.629164 | 1 | 0.327869 | 0.327869 |
| 1.737097 | 1 | 0.311475 | 0.311475 |
| 1.863982 | 1 | 0.295082 | 0.295082 |
| 1.91155 | 1 | 0.278689 | 0.278689 |
| 2.00222 | 1 | 0.262295 | 0.262295 |
| 2.344339 | 1 | 0.245902 | 0.245902 |
| 2.646382 | 1 | 0.229508 | 0.229508 |
| 2.830453 | 1 | 0.213115 | 0.213115 |
| 3.187143 | 1 | 0.196721 | 0.196721 |
| 3.416663 | 1 | 0.180328 | 0.180328 |
| 3.462855 | 1 | 0.163934 | 0.163934 |
| 3.583297 | 1 | 0.147541 | 0.147541 |
| 4.023514 | 1 | 0.131148 | 0.131148 |
| 4.380471 | 1 | 0.114754 | 0.114754 |
| 5.008613 | 1 | 0.098361 | 0.098361 |
| 6.546503 | 1 | 0.081967 | 0.081967 |
| 8.26769 | 1 | 0.065574 | 0.065574 |
| 9.691946 | 1 | 0.04918 | 0.04918 |
| 11.48465 | 1 | 0.032787 | 0.032787 |
| 26.62073 | 1 | 0.016393 | 0.016393 |
| Inf | 1 | 0 | 0 |

Discussion

Polyamines are statistically significantly elevated in plasmas of ovarian cancer cases in comparison to controls using two independent case-control cohorts. Of the measured polyamines, DAS exhibited the highest AUC for distinguishing cases from subjects presenting with benign pelvic masses or healthy controls. Importantly, a 3-marker panel consisting of DAS+N3AP+CA125 yielded improved classification performance in comparison to CA125 only, resulting in capturing early stage cases that were missed by CA125 alone in validation Set #2.

Prior studies have examined polyamine levels in urine and in one study urine polyamines were found to be elevated among subjects with ovarian cancer. Similar to this findings, DAS exhibited the best classification performance for delineating ovarian cancer cases from individuals with benign disease and was found to be associated with disease progression (Niemi 2017).

Polyamine biosynthesis is regulated by ODC1, the first enzyme in the polyamine pathway that mediates the decarboxylation of ornithine to generate putrescine, and by adenosylmethionine decarboxylase (AMD1) which decarboxylates S-adenosylmethionine to provide the aminopropyl donor for the conversion to spermidine and spermine. Generation of spermidine and spermine are mediated by two sequential aminopropyl transfer reactions via SRM and SMS. Intracellular polyamine levels are regulated by the enzymes spermidine/spermine N1-acetyltransferase (SAT1), which facilitates the acetylation of spermidine/spermine mediating cellular efflux, and the oxidases polyamine oxidase (PAOX) and spermine oxidase (SMOX). Analysis of transcriptomic data from the TCGA ovarian cancer dataset demonstrates that ODC1 and SMS are statistically significantly elevated in ovarian serous carcinomas in comparison to normal ovarian tissue, whereas PAOX was statistically significantly reduced, indicating that polyamine metabolism is elevated in ovarian cancer. Elevated polyamine metabolism manifests in increased biogenesis of acetylated polyamines, including DAS, and their subsequent accumulation in conditioned media of breast cancer cell lines.

ODC1, SRM and SMS are transcriptionally regulated by MYC. Consistent with the observation that siRNA-mediated knockdown of MYC resulted in a statistically significant reduction in mRNA levels of ODC1, SRM, and SMS in the serous ovarian cancer cell line SKOv3, thereby linking the plasma polyamine signature of the present disclosure to oncogenic MYC.

In conclusion, a MYC-driven polyamine signature has been identified that reflects early pathogenesis of ovarian cancer. Given the substantial interest in developing strategies for cancer detection and given the limited performance of CA125, validation of a polyamine signature for early stage ovarian cancer that complements CA125 provides supportive evidence for the utility of aberrant polyamine metabolism for cancer detection. These findings provide a basis for inclusion of the 3-marker panel on validation studies that encompass other biomarker candidates.

Example 6: Predictive Performance of Polyamines Plus the 3-Marker Panel Using Fixed Coefficients Currently, over 70% of patients with ovarian cancer (OvCa) present with advanced stage (III-IV) disease, with dismal 5-year survival rates of less than 30%. Survival rates up to 70-90% can, however, be achieved with conventional surgery and chemotherapy, when disease is localized to the ovary (stage I) or pelvis (Stage II). To-date, neither CA125 nor transvaginal sonography (TVS) alone has adequate sensitivity or specificity for general use in early detection. There is a need for additional marker(s) to detect early-stage ovarian cancer that would complement the performance shortcomings of CA125.

The predictive performance of polyamines, as well as the 3-marker polyamine panel, was tested using fixed coefficients in an independent dataset consisting of 219 newly-diagnosed ovarian cancer cases (59 stage I+II and 160 stage III+IV), 190 individuals with benign pelvic masses (BPM), and 409 healthy controls (Table 13).

TABLE 13

Patient and Tumor Characteristics for Independent Test Set.

| | Cases | Healthy Controls | Individuals |
|---|---|---|---|
| Number of Subjects | 219 | 409 | 190 |
| Age (mean +/− sd) | | | |
| Stage | | | |
| Stage I and II | 59 (26.9%) | — | — |
| Stage III and IV | 160 (73.1%) | — | — |

TABLE 13-continued

Patient and Tumor Characteristics for Independent Test Set.

| | Cases | Healthy Controls | Individuals |
|---|---|---|---|
| Histological Subtype, N | | | |
| Serous | 183 (83.6%) | — | —— |
| Non-Serous | 36 (16.4%) | — | —— |
| CA125 (U/mL) (median, $25^{th}/75^{th}$ Percentiles) | 292.5 (93.96-756.9) | 11.43 (9.11-16.06) | 18.95 (11.00-40.85) |

Individual performances of plasma polyamines for distinguishing OvCa cases from healthy controls ranged from 0.62-0.92; DAS yielded the highest predictive performance with an AUC of 0.92 (95% CI: 0.90-0.95) (Table 14).

TABLE 14

Predictive Performance of Indiidual Polyamines.

| Comparison | N, Cases | N, Controls | N3AP† | AcSpmd† | DiAcSpmd† | DAS† |
|---|---|---|---|---|---|---|
| Cases vs Controls | 219 | 409 | 0.62 (0.57-0.66) | 0.75 (0.71-0.79) | 0.73 (0.68-0.77) | 0.92 (0.90-0.95) |
| Early-Stage Cases vs Controls | 59 | 409 | 0.60 (0.53-0.68) | 0.69 (0.62-0.77) | 0.68 (0.61-0.75) | 0.88 (0.83-0.93) |
| Late-Stage Cases vs Controls | 160 | 409 | 0.62 (0.57-0.67) | 0.78 (0.84-0.82) | 0.74 (0.70-0.79) | 0.94 (0.91-0.96) |
| Cases vs BPM* | 219 | 190 | 0.62 (0.56-0.67) | 0.68 (0.63-0.73) | 0.70 (0.65-0.75) | 0.85 (0.81-0.88) |
| Early-Stage Cases vs BPM* | 59 | 190 | 0.60 (0.52-0.69) | 0.60 (0.52-0.69) | 0.66 (0.58-0.73) | 0.77 (0.70-0.84) |
| Late-Stage Cases vs BPM* | 160 | 190 | 0.62 (0.56-0.68) | 0.70 (0.65-0.76) | 0.72 (0.67-0.78) | 0.88 (0.84-0.91) |

*BPM: Benign Pelvic Masses;
†AUC (95% Confidence Interval);
Abbreviations:
N3AP- N-(3-acetamidopropyl)pyrrolidin-2-one;
AcSpmd- acetylspermidine;
DiAcSpmd- diacetylspermidine;
DAS- diacetylspermine The 3MP using fixed coefficients had a resultant AUC of 0.97 (95% CI: 0.95-0.99) for distinguishing OvCa cases from healthy controls and an AUC of 0.95 (95% CI: 0.91-0.98) when considering early stage OvCa cases (FIG. 9A-FIG. 9B). Importantly, at a pre-specified cutoff of 95% specificity, the 3-marker panel captured an additional 11.8% of OvCa cases that would otherwise have been missed by CA125 alone. Thus, the present study validated the utility of polyamines for early detection of ovarian cancer.

OTHER EMBODIMENTS

The detailed description set-forth above is provided to aid those skilled in the art in practicing the present disclosure. However, the disclosure described and claimed herein is not to be limited in scope by the specific embodiments herein disclosed because these embodiments are intended as illustration of several aspects of the disclosure. Any equivalent embodiments are intended to be within the scope of this disclosure. Indeed, various modifications of the disclosure in addition to those shown and described herein will become apparent to those skilled in the art from the foregoing description, which do not depart from the spirit or scope of the present inventive discovery. Such modifications are also intended to fall within the scope of the appended claims.

What is claimed is:

1. A method of determining the risk of a subject for harboring ovarian cancer and treating of ovarian cancer comprising the steps of:

a) measuring the levels of diacetylspermine (DAS), N-(3-acetamidopropyl) pyrrolidin-2-one (N3AP), and cancer antigen 125 (CA125) in a biological sample obtained from the subject; and b) comparing the levels of DAS, N3AP, and CA125 in said sample with a reference value corresponding to a healthy subject, wherein an altered amount of DAS, N3AP, and CA125 relative to said reference provides an indication that the subject harbors or is at risk of harboring ovarian cancer;

c) determining the subject has an altered amount of DAS, N3AP, and CA125 relative to said reference that indicates that the subject harbors or is at risk of harboring ovarian cancer; and d) administering a treatment for ovarian cancer chosen from one or more of:

administering an anticancer drug to the subject that is indicated as harboring or at risk of harboring ovarian cancer;

administering therapeutic radiation to the subject that is indicated as harboring or at risk of harboring ovarian cancer; and surgery for partial or complete surgical removal of cancerous tissue in the subject that is indicated as harboring or at risk of harboring ovarian cancer.

2. The method as recited in claim 1, further comprising measuring the levels of AcSpmd and/or DiAcSpmd.

3. The method as recited in claim 2, wherein:

the levels of DAS, N3AP, CA125, AcSpmd, and DiAcSpmd are elevated relative to the reference value; or wherein the levels of DAS, N3AP, CA125, AcSpmd, and DiAcSpmd are elevated relative to the corresponding levels in a biological sample obtained from a subject without ovarian cancer; or wherein the levels of DAS, N3AP, CA125, AcSpmd, and DiAcSpmd are elevated relative to the corresponding levels in a biological sample obtained from a subject with one or more benign pelvic masses.

4. The method as recited in claim 1, wherein the biological sample is derived from the blood of the subject.

5. The method as recited in claim 4, wherein the biological sample is serum.

6. The method as recited in claim 1, wherein the ovarian cancer is chosen from serous and non-serous; or wherein the ovarian cancer is epithelial in origin.

7. The method as recited in claim 6, wherein the non-serous ovarian cancer is chosen from endometrioid, mucinous, and clear cell carcinoma.

8. The method as recited in claim 1, wherein the ovarian cancer is early or advanced.

9. The method as recited in claim 1, wherein the subject has an amplification in c-myc.

10. The method as recited in claim 1, wherein the concentration of CA125 is determined by an immunoassay.

11. The method as recited in claim 10, wherein the immunoassay uses an anti-CA125 antibody or binding fragment thereof.

12. The method as recited in claim 1, wherein the concentration of at least one of DAS, N3AP, AcSpmd, and DiAcSpmd, or the concentrations of each of DAS, N3AP, AcSpmd, and DiAcSpmd, is determined by a method that comprises mass spectrometry or liquid chromatography, or both mass spectrometry and liquid chromatography.

13. The method as recited in claim 1, wherein:

the method provides improved sensitivity at a given specificity compared to a method assessing DAS alone, or to a method assessing CA125 alone; or wherein the method correctly identifies more early-stage ovarian cancers than a method assessing DAS or CA125 alone.

14. The method as recited in claim 13, wherein the method provides improved sensitivity at about 99% specificity.

15. The method as recited in claim 1, wherein the method is characterized by:

an AUC point estimate of greater than 0.82; or an AUC point estimate of about 0.84; or an AUC point estimate of about 0.97 for distinguishing ovarian cancer from healthy controls; or an AUC point estimate of about 0.95 for distinguishing early-stage ovarian cancer; or panel (b) has:

an AUC point estimate of greater than 0.82; or an AUC point estimate of about 0.84; or an AUC point estimate of about 0.97 for distinguishing ovarian cancer from healthy controls; or an AUC point estimate of about 0.95 for distinguishing early-stage ovarian cancer; or wherein DAS, N3AP, AcSpmd, DiAcSpmd, and CA125 are evaluated using fixed coefficients.

16. The method as recited in claim 1, wherein the method further comprises comparing the amount of DAS, N3AP, CA125, AcSpmd, and DiAcSpmd with a cutoff value comprising an AUC (95% CI) of from about 0.52 to about 0.95.

17. The method as recited in claim 16, wherein:

the cutoff value for N3AP comprises an AUC (95% CI) of at least 0.62; or the cutoff value for AcSpmd comprises an AUC (95% CI) of at least 0.75; or the cutoff value for DiAcSpmd comprises an AUC (95% CI) of at least 0.73; or the cutoff value for DAS comprises an AUC (95% CI) of at least 0.92.

* * * * *